US011326146B2

(12) United States Patent
Gilligan et al.

(10) Patent No.: US 11,326,146 B2
(45) Date of Patent: May 10, 2022

(54) LOW SUGAR SPERM MEDIA AND COMPOSITIONS

(71) Applicant: Inguran, LLC, Navasota, TX (US)

(72) Inventors: Thomas B. Gilligan, College Station, TX (US); Ramakrishnan Vishwanath, Hamilton (NZ); Kilby Willenburg, Madison, WI (US)

(73) Assignee: Inguran, LLC, Navasota, TX (US)

( * ) Notice: Subject to any disclaimer, the term of this patent is extended or adjusted under 35 U.S.C. 154(b) by 0 days.

(21) Appl. No.: 14/947,912

(22) Filed: Nov. 20, 2015

(65) Prior Publication Data

US 2016/0145568 A1 May 26, 2016

Related U.S. Application Data

(60) Provisional application No. 62/082,445, filed on Nov. 20, 2014.

(51) Int. Cl.
*C12N 5/076* (2010.01)
*A61D 19/02* (2006.01)

(52) U.S. Cl.
CPC .............. *C12N 5/061* (2013.01); *A61D 19/02* (2013.01); *C12N 2500/34* (2013.01)

(58) Field of Classification Search
None
See application file for complete search history.

(56) References Cited

U.S. PATENT DOCUMENTS

| | | | |
|---|---|---|---|
| 3,791,384 A | 2/1974 | Richter et al. | |
| 9,140,688 B2 * | 9/2015 | Evans | G01N 21/6428 |
| 9,581,587 B2 * | 2/2017 | Evans | G01N 21/6428 |
| 2004/0073964 A1 | 4/2004 | Ellington | |
| 2005/0064383 A1 * | 3/2005 | Bashkin | G01N 15/1456 435/4 |
| 2005/0112541 A1 | 5/2005 | Durack | |
| 2006/0270033 A1 * | 11/2006 | Rutledge | A01N 1/0226 435/325 |
| 2007/0117086 A1 | 5/2007 | Evans | |
| 2010/0068809 A1 * | 3/2010 | Herickhoff | A61K 36/185 435/375 |
| 2011/0076712 A1 * | 3/2011 | Gilligan | G01N 15/1404 435/29 |
| 2011/0217722 A1 * | 9/2011 | Durack | C12N 5/0612 435/29 |
| 2013/0084558 A1 * | 4/2013 | Evans | G01N 21/6428 435/2 |
| 2013/0183656 A1 | 7/2013 | Lenz | |
| 2014/0234833 A1 * | 8/2014 | Evans | G01N 21/6428 435/6.1 |

FOREIGN PATENT DOCUMENTS

| | | | |
|---|---|---|---|
| WO | WO-9013303 A1 * | 11/1990 | ............ A61K 35/52 |
| WO | 0241906 A2 | 5/2002 | |
| WO | 03096799 A2 | 11/2003 | |
| WO | WO 2004/072224 A2 * | 8/2004 | |
| WO | 2005094852 A2 | 10/2005 | |
| WO | 2005095590 A2 | 10/2005 | |
| WO | 2005095960 A1 | 10/2005 | |
| WO | 2006029653 A1 | 3/2006 | |
| WO | 2009086191 A1 | 7/2009 | |
| WO | WO 2012/167151 A1 * | 12/2012 | |

OTHER PUBLICATIONS

Parrish et al. Biology of Reproduction (1989) 41: 683-69.*
Tsujii et al. Reproductive Med. Biol. (2006) 5: 255-261 (Year: 2006).*
Nagai et al. J. Pharm. Dyn. (1982) 5: 654-567 (Year: 1982).*
Davis C. and Reeves "High Value Opportunities From the Chicken Egg." A report for the Rural Industries Research and Development Corporation. 2002.
Unal, M. B. et al. "Influence of Sugars with Glycerol on Post-thaw Motility of Bovine Spermatozoa in Straws." J Dairy Sci 61. pp. 83-89. 1978.
Wall, R. J. and Foote, R. H. "Fertility of Bull Sperm Frozen and Stored in Clarified Egg Yolk-Tris-Glycerol Extender." J Dairy 82. pp. 817-821. 1999.
Pace, M. M. and Graham, E. F. "Components in Egg Yolk Which Protect Bovine Spermatozoa During Freezing." Journal of Animal Science, vol. 39, No. 6, pp. 1144-1149. 1974.
Foote, R. H. "Fertility of Bull Semen at High Extension Rates in Tris-Buffered Extenders." Journal of Dairy Science. vol. 53, No. 10. pp. 1475-1477. 1970.
Shannon, P. "Factors Affecting Semen Preservation and Conception Rates in Cattle." J. Reprod. Fert. 54. pp. 519-527. 1978. (Date is incorrectly indicated as 1798 on the document.).
Juyena, N. and Stelletta, C. "Seminal Plasma: An Essential Attribute to Spermatozoa." Journal of Andrology, vol. 33, No. 4, pp. 536-551. Jul./Aug. 2012.
Crabo, B. G. et al. "Effect of Some Buffers on Storage and Freezing of Boar Spermatozoa." Journal of Animal Science, vol. 35, No. 2, pp. 377-382. 1972.
Del Olmo et al. "Handling of Boar Spermatozoa During and After flow Cytometric Sex-Sorting Process to Improve their in Vitro Fertilizing Ability." Theriogenology 80 (2013) pp. 350-356.
Rodriguez-Gil, JE. "Mammalian Sperm Energy Resources Management and Survival during Conservation in Refrigeration." Reprod Dom Anim 41 (Suppl. 2), pp. 11-20 (2006).
Kamp, G. "Energy Metabolism and Intracellular pH in Boar Spermatozoa." Reproduction (2003) 126, pp. 517-525.

(Continued)

*Primary Examiner* — Susan M Hanley

(74) *Attorney, Agent, or Firm* — Ryan Christensen; Hashim Rahman

(57) ABSTRACT

The present invention relates to compositions comprising low sugar media, the methods of using these compositions to reduce trauma and stress on processed animal sperm, the resulting sperm and embryo products, and the methods of use of these products to increase the quality, quantity and viability of progeny and improved rates of births in animals.

9 Claims, 19 Drawing Sheets

(56) References Cited

OTHER PUBLICATIONS

Medrano, A. et al. "Variations in the Proportion of Glycolytic/Non-glycolytic Energy Substrates Modulate Sperm Membrane Integrity and Function in Diluted Boar Samples Stored at 15-17° C." Reprod Dom Anim 40, pp. 448-453 (2005).
Rath, D. "Production of Piglets Preselected for Sex Following In Vitro Fertilization with X and Y Chromosome-Bearing Spermatozoa Sorted be Flow Cytometry." Theriogenology, 47, 1997. pp. 795-800.
Rath, D. "In Vitro Production of Sexed Embryos for Gender Preselection: High-Speed Sorting of X-Chromosome-Bearing Sperm to Produce Pigs After Embryo Tranfer." J. Anim. Sci. 1999. 77, pp. 3346-3352.
Salisbury, G. W. et al. "Substiate-Free Epididymal-Like Bovine Spermatozoa." J. Reprod. Fertil. (1963) 6, 3pp. 351-359.
Marin, Silvia et al. "Metabolic Strategy of Boar Spermatozoa Revealed by a Metabolomic Characterization." FEBS Letters 554 (2003) pp. 342-346.
Johnson, L. A. "Use of Boar Spermatozoa for Artificial Insemination Iii. Fecundity of Boar Spermatozoa Stored in Beltsville Liquid and Kiev Extenders for Three Days at 18 C." Journal of Animal Science, vol. 54, No. 1, 1982.
Gil, Maria, et al. "Pentoxifylline Added to Freezing or Post-Thaw Extenders Does not Improve the Survival or In Vitro Fertilising Capacity of Boar Spermatozoa." Reproduction (2010) 139 pp. 557-564.
Hu, J.-H. et al. "Effects of Trehalose Supplementation on Semen Quality and Oxidative Stress Variables in Frozen-Thawed Bovine Semen." J Anim Sci 2010, 88: pp. 1657-1662.
Aboagla, Eiman M.-E. et al. "Trehalose-Enhanced Fluidity of the Goat Sperm Membrane and Its Protection During Freezing." Biology of Reproduction 69, 1245-1250 (2003).
Ahmed, Ejaz et al. "Trehalose as a Cryoprotective Agent for the Sperm Cells: A Mini Review." Animal Health, Prod. and Hyg. (2012) 1(2): 123-129.
Martinez, EA, et al. "An update on Reproductive Technologies with Potential Short-Term Application in Pig Production." Reprod Dom Anim 40, pp. 300-309 (2005).
Rath, D. et al. "Birth of Female Piglets Following Intrauterine Insemination of a Sow Using Flow Cytometrically Sexed Boar Semen." Veterinary Record (2003) 152, pp. 400-401.
Vazquez, Juan Maria et al. "Birth of Piglets After Deep Intrauterine Insemination with Flow Cytometrically Sorted Boar Spermatozoa." Theriogenology 59 (2003) pp. 605-1614.
Blair, R. M. et al. "Peri-oestrous Hormone Profiles, Embryonic Survival and Variation in Embryonic Development in Gilts and Primiparous Sows." Journal of Reproduction and Fertility (1994) 101, pp. 167-173.
Bolarin, Alfonso et al. "Dissimilarities in Sows' Ovarian Status at the Insemination Time Could Explain Differences in Fertility Between Farms When Frozen-Thawed Semen is Used." Theriogenology 65 (2006) pp. 669-680.
Wongtawan, Tuempong et al. "Fertility After Deep Intra-Uterine Artificial Insemination of Concentrated Low-Volume Boar Semen Doses." Theriogenology 65 (2006) pp. 773-787.
Roca, Jordi, et al. "Fertility of Weaned Sows After Deep Intrauterine Insemination with a Reduced Number of Frozen-Thawed Spermatozoa." Theriogenology 60 (2003) pp. 77-87.
Bathgate, R. et al. "Field Fertility of Frozen-Thawed Boar Sperm at Low Doses Using Non-Surgical, Deep Uterine Insemination." Animal Reproduction Science 103 (2008) pp. 323-335.
Garner, Duane L. "Flow Cytometric Sexing of Mammalian Sperm." Theriogenology 65 (2006) pp. 943-957.
Rath, D. et al. "Application and Commercialization of Flow Cytometrically Sex-Sorted Semen." Reprod Dom Anim 43 (Suppl. 2), 338-346 (2008).
Garcia, E. M. et al. "Improving the Fertilizing Ability of Sex Sorted Boar Spermatozoa." Theriogenology 68 (2007) pp. 771-778.

Garner, Diane L. "Viability Assessment of Mammalian Sperm Using SYBR-14 and Propidium Iodide." Biology of Reproduction 53, 276-284 (1995).
Gosalvez, LF et al. "Assessment of suitable porcine semen for freezing, according to the ejaculate characteristics in the Iberico x Landrace breed." Reprod Domest Anim. Oct. 2002; 37(5): 282-4.
Dally, Martin, et al. "Wool Production School." 1992.
Rodriguez-Martinez, Heriberto et al. "Advances in Boar Semen Cryopreservation." vol. 2011 (2011), Article ID 396181, 5 pages. 2010. http://www.hindawi.com/journals/vmi/2011/396181/.
Medeiros, C. M. O. et al. "Current Status of Sperm Cryopreservation: Why Isn't It Better?" Theriogenology 57:327-344, 2002.
Guthrie, H. D. et al. "Impact of Storage Prior to Cryopreservation on Plasma Membrane Function and Fertility of Boar Sperm." Theriogenology 63 (2005) pp. 396-410.
IMV Technologies Catalog "Biotechnologies for pig reproduction", www.imv-technologies.com, 28pp. 2012.
Martinez, E.A. , et al. "Incidence of Unilateral Fertilizations after Low Dose Deep Intrauterine Insemination in Spontaneously Ovulating Sows under Field Conditions", Reproduction in Domestic Animals, vol. 41, Issue1, pp. 41-47, Feb. 2006.
Klinc, P., et al., "Reduction of Oxidative Stress in Bovine Spermatozoa During Flow Cytometric Sorting", Reproduction in Domestic Animals, vol. 42, pp. 63-67 (2007).
Knox, R., et al., "An update on North American Boar stud practices", Theriogenology, vol. 70, pp. 1202-1208, (2008).
Fantinati, P., et al., "Laparoscopic insemination technique with low numbers of spermatozoa in superovulated prepuberal gilts for biotechnological application", Theriogenology, Feb. 2005; 63(3): 806-17.
Martelli, A., et al., "Blood vessel remodeling in pig ovarian follicles during the periovulatory period: an immunohistochemisty and SEM-corrosion casting study", Reproductive Biology and Endocrinology, 2009, 7:72 (2009).
Martinez, E.A. , et al., "Minimum number of spermatozoa required for normal fertility after deep intrauterine insemination in non-sedated sows", Reproduction, Jan. 1, 2002, 123 163-170.
Vazquez, J.M., et al. "New developments in low-dose insemination technology", Theriogenology, vol. 70(8): Nov. 2008, pp. 1216-1224.
Rath et al., "Low Dose Insemination Technique in the Pig" IVth Intl Conference on Boar Semen Preservation, Beltsville, Maryland, 2000, pp. 115-118.
Rath, D., "Low Dose Insemination in the Sow—A Review" Reprod Dom Anim, 2002, 37, 201-205.
Rathi, R. et al., "Evaluation of In Vitro Capacitation of Stallion Spermatozoa." Biology of Reproduction 65, 462-470 (2001).
Tummaruk, P., et al., "Distribution of Spermatozoa and Embryos in the Female Reproductive Tract after Unilateral Deep Intra Uterine Insemination in the Pig", Reproduction in Domestic Animals, vol. 42, Issue 6, pp. 603-609, Dec. 2007.
Roca, J. et al., "Survival and Fertility of Boar Spermatozoa After Freeze-Thawing in Extender Supplemented With Butylatd Hydroxytoluene", Journal of Andrology, vol. 25, No. 3 pp. 397-405 (2004).
Mathur, P.K., "Effective selection to expedite your genetic progress" Canadian Centre for Swine Improvement Inc., 2002, http://www.ccsi.ca/main.cfm?target_page=select, 7 pages.
Spinaci, M., "Sperm Sorting Procedure Induces a Redistribution of Hsp70 but Not Hsp60 and Hsp90 in Boar Spermatozoa", Journal of Andrology, vol. 70, No. 6, pp. 899-907 (2006).
Martinez, E.A. , et al., "Successful non-surgical deep intrauterine insemination with small numbers of spermatozoa in sows", Reproduction—online Aug. 2001, 122 289-296.
Tuncer, Purhan Barbaros, et al. "Effects of Different Doses of Trehalose Supplementation in Egg Yolk Extender in Frozen-Thawed Angora Buck Semen." 2013. http://dx.doi.org/10.1016/j.smallrumres.2013.04.012.
Bolarín A. et al. "Use of Frozen-Thawed Semen Aggravates the Summer-Autumn Infertility of Artificially Inseminated Weaned Sows in The Mediterranean Region."J Anim Sci 2009, 87:3967-3975.

(56) References Cited

OTHER PUBLICATIONS

Vasquez, J.M., et al., "Sex-sorting sperm by flow cytometry in pigs: Issues and perspectives", Theriogenology, vol. 71, pp. 80-88 (2009).
Van Wienen et al., "Single Layer Centrifugation with Androcoll-P Can Be Scaled-Up to Process Larger Volumes of Boar Semen." ISRN Veterinary Science, vol. 2011, Article ID 548385, 8 pages.
Bucci et al. "Capacitation-like Changes in Sex-Sorted Boar Spermatozoa." Poster Abstract P47, Reprod Dom Anim 46 (Suppl. 3), pp. 91 (2011).
Cinar et al. "Media Supplementation With Seminal Plasma Proteins Improves Quality of Bold Sorted Cryopreserved Bovine Sperm." Poster Abstract P60, Reprod Dom Anim 60 (Suppl. 3), pp. 95 (2011).
Del Olmo et al. "The Effect of Butylated Hydroxytoluene on the Functionality of Boar Spermatozoa Undergoing Sex Sorting and Cryopreservation." Poster Abstract P73, Reprod Dom Anim 73 (Suppl. 3), pp. 98 (2011).
Fani Maleki, A. "Determination of Sex Ratio in Bovine Semen By Quantitative Sybr Green Real Time PCR." Poster Abstract P89, Reprod Dom Anim 89 (Suppl. 3), pp. 103 (2011).
Parrilla et al. "Post-Thaw Quality of Boar Semen Frozen at Low Sperm Concentration." Poster Abstract P208, Reprod Dom Anim 89 (Suppl. 3), pp. 137 (2011).
Knox "The Current Value of Frozen-Thawed Boar Semen for Commercial Companies." Reprod Dom Anim 46 (Suppl 2), 4-6 (2011).
Waberski et al. "Assessment of Storage Elects in Liquid Preserved Boar Semen." Reprod Dom Anim 46 (Suppl 2), 45-48 (2011).
Roca et al. "Approaches Towards Efficient Use of Boar Semen in the Pig Industry." Reprod Dom Anim 46 (Suppl 2), 79-83 (2011).
Parrilla et al. "Membrane Lipid Peroxidation in Boar Spermatozoa Subjected to Different Handlings." Abstract OC 15, Reprod Dom Anim 46 (Suppl 2), pp. 89 (2011).
Zeng et al. "Sex-Preselected Piglets Derived From Surgical Artificial Insemination With Sexed Sperm." Abstract P53, Reprod Dom Anim 46 (Suppl 2), pp. 109 (2011).
International Search Report and Written Opinion dated Feb. 9, 2016 issued in related international application No. PCT/US15/61922.
Trigal et al. "Optimizing Protocols for In Vitro Fertilization with Bovine Sex-Sorted Sperm." Abstract OC16. Reprod Dom Anim 45(Suppl. 2), pp. 83 (2010).
Del Olmo et al. "Influence of Seminal Plasma and Heterodimer PSP-I/PSP-II on the Kinematic Shanges of Boar Sperm Undergoing Sex Sorting and Cryopreservation" Abstract P58. Reprod Dom Anim 45(Suppl. 2), pp. 83 (2010).
Bolarin A. et al. "Reproductive performance of sows returned to estrus after a DUI insemination." Poster Abstract P66. Reprod Dom Anim. 45(Suppl. 3), pp. 79. (2010).
Extended European Search Report dated Mar. 26, 2018 issued in related EP Application No. 15860335.7.
New Zealand Examination Report dated Jun. 8, 2018 issued in related NZ Application No. 732071.
European Examination Report dated Feb. 20, 2019 issued in related EP Application No. 15860335.7.
New Zealand Examination Report dated Jan. 10, 2019 issued in related NZ Application No. 732071.
New Zealand Examination Report dated Apr. 18, 2019 in related NZ Appl. No. 732071.
Canadian Office Action dated Apr. 29, 2020 in related CA Appl. No. 2,968,414.
European Office Action dated Mar. 31, 2021 in related EP Appl. No. 15860335.7.
European Examination Report dated Mar. 4, 2020 in related EP Appl. No. 15860335.7.

* cited by examiner

LOW SUGAR SPERM MEDIA AND COMPOSITIONS

The present invention relates to compositions comprising low sugar media, the methods of using these compositions to reduce trauma and stress on processed animal sperm, the resulting sperm and embryo products, and the methods of use of these products to increase the quality, quantity and viability of progeny and improved rates of births in animals.

BACKGROUND

Assisted reproductive technology (ART) includes such techniques as in vitro fertilization (IVF), artificial insemination (AI), intracytoplasmic sperm injection (ICSI) (other techniques using enucleated cells) and multiple ovulation and embryo transfer (MOET) (as well as other embryo transfer techniques) and is used across the animal kingdom. ART methods are generally expensive, time consuming and marginally successful given the inherent fragility of gametes when outside of their natural environments. Furthermore, the use of ART within the animal breeding industry in a commercially feasible manner is additionally challenging due to the limited availability of genetically desirable gametes (sperm or oocytes). One way to lower the cost of ART and to improve its commercial feasibility is to increase the efficiency of the involved processes by improving the viability and overall quality of gametes used in ART. Although there has been a growing interest in this field over the course of the last decade or so, there still remains a strong need to increase the overall quality of gametes for use in ART, especially when breeding focuses on pre-natal gender selection, including improving gametes viability, motility and fertility, as well as other longevity characteristics.

For example, in conventional AI, one problem limiting its commercial application in certain species is the need to use extremely high number of sperm per AI dose to ensure successful fertilization currently. In swine in particular, the need for improved sperm quality is especially strong since the typical dose of boar sperm required for successful fertilization using conventional artificial insemination techniques, such as intra-cervical insemination, is currently $1 \times 10^9$ sperm to $3 \times 10^9$ sperm.

Processing gametes such as flushed oocytes or sperm, both conventional and sex sorted, before their use in ART may add a tremendous amount of stress on the gamete cell(s) and often negatively impacts their cellular integrity and membrane structure, which in turn may be reflected in decreased viability, motility and fertility. An example of processing gametes prior to their use in ART is the sorting of sperm based on sex (known as "gender enrichment" or "sex sorting"), which is a now commonly used procedure to minimize wasted births of the wrong sex for selective breeding in the livestock industry. In some species, however, it is still cost prohibitive and can represent a financial risk to those with smaller breeding herds. Sex sorting includes processes that physically separate X and Y bearing sperm from each other into separate subpopulations, as well as processes in which sperm bearing the undesired sex chromosome in a sperm sample are selectively killed, compromised, disabled, rendered immotile, or otherwise rendered infertile by, for example, laser ablation/photo damage techniques to render a gender enriched population of sperm.

The sex sorting process severely stresses and damages the cells and produces a low percentage of useful sperm, which although capable of fertilizing matured oocytes, may have reduced viability, motility and fertility compared to unprocessed cells. Typically, sex sorting involves many harsh steps including but not limited to: the initial collection and handling of sperm ejaculate, which naturally starts to deteriorate rapidly upon collection; the staining of sperm, which involves binding of an excitable dye to the DNA or a harmful membrane selection procedure; the physical sorting of the sperm using high energy fluorescence that physically energizes the dye that is bound to the DNA, forced orientation through a narrow orifice, and application of an electrical charge to the cell; the physical collection of the cells into a receiving container, which often shocks the fragile cell upon contact; the osmotic stresses associated with dilution of the sperm droplet in collection media; and the storage of the sorted sperm usually by freezing, which is well known to raise havoc with the cell's membrane systems. Each step places the processed sperm under abnormal stress that diminishes the overall motility, viability and/or fertility of the sperm. The result can lead to less efficient samples for use in ART, such as IVF and AI, and other types of subsequent or further processing.

Even non-sorted processed sperm exhibits significant losses in fertility, viability and motility when being collected, handled and transported without freezing, and noticeably experiences significant stress when mixed with cryoprotectant and frozen and thawed. Many in the field have tried to improve methods for the use on unsorted, conventional semen to minimize loss in the handling processes associated with in vitro handling, preservation and use of semen samples.

Regardless of the processing, sperm lose their potential to fertilize when exposed to: elevated temperatures, abnormal buffers, stains, altered pH systems, physical pressurized orientation as when forced through a nozzle or when oscillated to form drops in a flow cytometer, radiation used to illuminate the DNA binding dye, physical stressors associated with separation and collection techniques, cryoprotectants, freezing, thawing and micromanipulation by the handler.

There remains a continuing need to improve current methods of ART to reduce the cost and to make the procedures more dependable and commercially feasible to those on a restricted budget, especially for smaller breeders for whom sex-selection breeding may be a high risk and expensive option. One way in which researchers have attempted to increase the viability, motility and/or fertility of gametes for use in ART is through the use of specialized media used to store and/or process gametes. For example, in the sex sorting process, sperm is typically collected in an extender, stained in a staining solution, sorted with a sheath fluid and finally collected in a catch media. Exposure to each of these types of media may have beneficial, or deleterious, effects on the sperm depending on the constituents of the media. For example, current sperm media used in sex sorting typically include high concentrations of one or more sugar additives, which are often added as an energy source, but may actually increase the sensitivity of sperm to the stresses associated with processing and sorting.

While use of existing media has allowed commercially viable production of sex sorted sperm in certain species, there remains the need to further increase the viability, motility and fertility of sex sorted sperm in order to increase efficiency and lower costs. Furthermore, while sex sorting sperm is currently commercially viable in certain species, such as bovines, in other species, inefficiencies in the process preclude sex sorting in a commercially viable manner at present. Accordingly, there is a significant need for improved media for use in processing and sorting sperm.

SUMMARY OF THE INVENTION

A broad object of the present invention is to provide improvements in the motility, viability, fertility and overall integrity of processed sperm, particularly sperm that undergo analysis and/or sex sorting. In order to achieve such improvements, one aspect of the present invention broadly encompasses compositions comprising low sugar media and the use of such compositions during the cell sorting process. Other aspects of the invention encompass methods of using sperm processed with low sugar media in various ART procedures, including but not limited to, IVF, AI, ICSI and MOET.

A further aspect of the instant invention relates to the discovery that the use of low sugar media allows for freezing and thawing of media comprising a protein source, such as egg yolk, without any deleterious effects relative to media that has not been frozen. In fact, the use of such frozen-thawed media has been shown by the inventors to actually increase the viability of processed sperm. This discovery allows for the shipping of media in a frozen state to a destination where it can then be thawed and used. The ability to ship frozen media with perishable components such as egg yolk and other protein sources also allows for the standardization of media across various geographically separate lab facilities, which can yield an improvement in end product consistency and quality control among labs. A further aspect of the present invention broadly encompasses the use of such frozen-thawed low sugar media comprising a protein source, such as egg yolk, during the cell sorting process.

The term "sugar" as used herein refers to mono- or di-saccharides that are generally metabolized by mammalian sperm, e.g., glucose and fructose. The term "sugar additive" as used herein means sugar that is added to a media as a discrete compound and not as a naturally occurring component of another additive in the media such as egg yolk, seminal fluid or milk.

In certain embodiments of the invention, low sugar media comprises less than about 50 mM, 45 mM, 40 mM, 35 mM, 30 mM, 25 mM, 20 mM, 19 mM, 18 mM, 17 mM, 16.5 mM, 16 mM, 15.5 mM, 15 mM, 14.5 mM, 14 mM, 13.5 mM, 13 mM, 12.5 mM, 12 mM, 11.5 mM, 11 mM, 10.9 mM, 10.8 mM, 10.7 mM, 10.6 mM, 10.5 mM, 10.4 mM, 10.3 mM, 10.2 mM, 10.1 mM, 10.0 mM, 10 mM, 9.75 mM, 9.5 mM, 9.25 mM, 9.0 mM, 9 mM, 5 mM of sugar additive. In other embodiments of the invention, low sugar media comprises about 1-5 mM, 5-10 mM, 10-15 mM, 15-20 mM, 20-25 mM, 25-30 mM, 35-40 mM, or 45-50 mM of sugar additive. In further embodiments of the invention, low sugar media comprises about 1-5 mM, 1-10 mM, 1-15 mM, 1-20 mM, 1-25 mM, 1-30 mM, 1-35 mM, 1-40 mM, 1-45 mM, or 1-50 mM of sugar additive. In yet further embodiments of the invention, low sugar media comprises about 0.1 ppm to about 5 mM, about 0.1 ppm to about 10 mM, about 0.1 ppm to about 15 mM, about 0.1 ppm to about 20 mM, about 0.1 ppm to about 25 mM, about 0.1 ppm to about 30 mM, about 0.1 ppm to about 35 mM, about 0.1 ppm to about 40 mM, about 0.1 ppm to about 45 mM, or about 0.1 ppm to about 50 mM of sugar additive. In other embodiments of the invention, low sugar media comprises about 1 mM, 2 mM, 3 mM, 4 mM, 4.1 mM, 4.2 mM, 4.3 mM, 4.4 mM, 4.5 mM, 4.6 mM, 4.7 mM, 4.8 mM, 4.9 mM, 5 mM, 5.0 mM, 5.1 mM, 5.2 mM, 5.3 mM, 5.4 mM, 5.5 mM, 5.6 mM, 5.7 mM, 5.8 mM, 5.9 mM, 6 mM, 7 mM, 8 mM, 9 mM, 9.1, 9.2, 9.3, 9.4, 9.5, 9.6, 9.7, 9.8, 9.9, 10 mM, 10.0, 10.1, 10.2, 10.3, 10.4, 10.5, 10.6, 10.7, 10.8, 10.9, 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, or 50 mM of sugar additive. In a further embodiment of the invention, low sugar media comprises about 1-10 mM, 2-9 mM, 3-6 mM, 4-6 mM, or 4-5 mM of sugar additive. In yet another embodiment of the invention, low sugar media comprises about 5-15 mM, 6-14 mM, 7-13 mM, 8-12 mM, 9-11 mM or 9-10 mM of sugar additive. In yet another embodiment of the invention, low sugar media comprises no sugar additive or at most, trace amounts of sugar additive (i.e., no more than 0.1-20 ppm of sugar additive).

In certain embodiments of the invention, low sugar media comprises less than about 50 mM, 45 mM, 40 mM, 35 mM, 30 mM, 25 mM, 20 mM, 19 mM, 18 mM, 17 mM, 16.5 mM, 16 mM, 15.5 mM, 15 mM, 14.5 mM, 14 mM, 13.5 mM, 13 mM, 12.5 mM, 12 mM, 11.5 mM, 11 mM, 10.9 mM, 10.8 mM, 10.7 mM, 10.6 mM, 10.5 mM, 10.4 mM, 10.3 mM, 10.2 mM, 10.1 mM, 10.0 mM, 10 mM, 9.75 mM, 9.5 mM, 9.25 mM, 9.0 mM, 9 mM, 5 mM of sugar. In other embodiments of the invention, low sugar media comprises about 1-5 mM, 5-10 mM, 10-15 mM, 15-20 mM, 20-25 mM, 25-30 mM, 35-40 mM, or 45-50 mM of sugar. In further embodiments of the invention, low sugar media comprises about 1-5 mM, 1-10 mM, 1-15 mM, 1-20 mM, 1-25 mM, 1-30 mM, 1-35 mM, 1-40 mM, 1-45 mM, or 1-50 mM of sugar. In yet further embodiments of the invention, low sugar media comprises about 0.1 ppm to about 5 mM, about 0.1 ppm to about 10 mM, about 0.1 ppm to about 15 mM, about 0.1 ppm to about 20 mM, about 0.1 ppm to about 25 mM, about 0.1 ppm to about 30 mM, about 0.1 ppm to about 35 mM, about 0.1 ppm to about 40 mM, about 0.1 ppm to about 45 mM, or about 0.1 ppm to about 50 mM of sugar. In other embodiments of the invention, low sugar media comprises about 1 mM, 2 mM, 3 mM, 4 mM, 4.1 mM, 4.2 mM, 4.3 mM, 4.4 mM, 4.5 mM, 4.6 mM, 4.7 mM, 4.8 mM, 4.9 mM, 5 mM, 5.0 mM, 5.1 mM, 5.2 mM, 5.3 mM, 5.4 mM, 5.5 mM, 5.6 mM, 5.7 mM, 5.8 mM, 5.9 mM, 6 mM, 7 mM, 8 mM, 9 mM, 9.1, 9.2, 9.3, 9.4, 9.5, 9.6, 9.7, 9.8, 9.9, 10 mM, 10.0, 10.1, 10.2, 10.3, 10.4, 10.5, 10.6, 10.7, 10.8, 10.9, 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, or 50 mM of sugar. In a further embodiment of the invention, low sugar media comprises about 1-10 mM, 2-9 mM, 3-6 mM, 4-6 mM, or 4-5 mM of sugar. In yet another embodiment of the invention, low sugar media comprises about 5-15 mM, 6-14 mM, 7-13 mM, 8-12 mM, 9-11 mM or 9-10 mM of sugar. In another embodiment of the invention, low sugar media comprises no sugar or at most, trace amounts of sugar (i.e., no more than 0.1-20 ppm of sugar).

In certain embodiments of the invention, sex sorting of sperm may be accomplished using any process or device known in the art for cell analysis, sorting and/or population enrichment including but not limited to use of a flow cytometer or use of a microfluidic chip. As contemplated herein, sex sorting in addition to encompassing techniques for physically separating X and y bearing sperm from each other as with droplet sorting and fluid switching sorting, also encompasses techniques for gender enrichment in which sperm bearing the undesired sex chromosome are killed, immobilized, or otherwise rendered infertile, such as by use of laser ablation/photo damage techniques.

In one embodiment of the invention, low sugar media may comprise one or more buffers, including but not limited to carbonates, phosphates, citrates, acetates, lactates, and combinations thereof, or a solution containing a salt, a carbohydrate, or a combination thereof can be employed in some of the embodiments of the invention, such as, but not limited to, Tris, TES, HEPES, TALP, TCA, PBS, citrate, milk and derivatives thereof, as discussed in detail in U.S. Pat. No. 7,208,265 the contents of which is hereby incorporated by reference in its entirety.

In certain embodiments, low sugar media may comprise one or more chelators, including but not limited to, deferoxamine, deferasirox, penicillamine, alpha lipoic acid, DMPS, DMSA, dimercaprol and aminopolycarboxylic acids (complexones), including but not limited to Fura-2, IDA, NTA, EDTA, DTPA, EGTA, BAPTA, NOTA, DOTA and nicotianamine, and derivatives thereof.

In other embodiments, low sugar media may comprise one or more "organic stress reducing" agents (OSRs), which may comprise an antioxidant, a vitamin or other organic molecule involved directly or indirectly in modulating physiological stresses in the cell. In certain embodiments, low sugar media may comprise one or more OSRs, each in the concentration range of 0.01 mg/ml to 5 mg/ml. Various OSRs can be used in the context of the current invention, including but not limited to: catalase, superoxide dismutase (SOD), SOD mimics, glutathione, glutathione reductase, glutathione peroxidase, pyruvate, mercaptoethanol, butylated hydroxytoluene (BHT), lipoic acid, flavins, quinones, vitamin K (and related vitamers), vitamin B12 (and related vitamers), with 'vitamers' defined as compounds having the same vitamin activity (such as cobalamin, cyanocobalamin, methylcobalamin, adenosylcobalamin, hydroxocobalamin, and pseudo-B12), vitamin E (including its vitamers, tocopherols ($\alpha$, $\beta$, $\gamma$), tocotrienols, and $\alpha$-tocopheryl), alpha-ketoglutarate (also known as $\alpha$-KG, AKG or oxo-glutarate) and various biological forms of AKG (such as arginine, aspartate, lysine, and similar derivatives), other compounds that regulate nitric oxide in the cell including malondialdehyde (MDA) and asymmetric dimethylarginine (ADMA), and biologically active derivatives thereof.

Certain embodiments of the invention utilize concentrations of OSRs selected from the following ranges: 0.01 to 5.0 mg/ml; 0.01 to 0.25 mg/ml; 0.01 to 0.5 mg/ml; 0.01 to 1 mg/ml; 0.01 to 2.5 mg/ml; 0.01 to 5 mg/ml; 0.05 to 0.1 mg/ml; 0.05 to 1.0 mg/ml; 0.05 to 2.5 mg/ml; 0.1 to 0.25 mg/ml; 0.1 to 0.5 mg/ml; 0.1 to 1 mg/ml; 0.1 to 2.5 mg/ml; 0.1 to 5 mg/ml; 0.15 to 0.45 mg/ml; 0.15 to 0.5 mg/ml; 0.25 to 0.35 mg/ml; 0.25 to 0.5 mg/ml; 0.25 to 1 mg/ml; 0.25 to 2.5 mg/ml; 0.25 to 5 mg/ml; 0.35 to 0.5 mg/ml; 0.35 to 1 mg/ml; 0.35 to 2.5 mg/ml; 0.35 to 5 mg/ml; 0.5 to 1 mg/ml; 0.5 to 2.5 mg/ml; 0.5 to 5 mg/ml; 1 to 2.5 mg/ml; 1 to 5 mg/ml; about 0.05 mg/ml; about 0.1 mg/ml; about 0.15 mg/ml; about 0.25 mg/ml; about 0.35 mg/ml; about 0.45 mg/ml; and about 0.5 mg/ml.

In other embodiments, low sugar media may comprise one or more tricarboxylic acid cycle intermediates, including but not limited to, pyruvate, acetyl-CoA, citrate, isocitrate, $\alpha$-ketoglutarate, succinyl-CoA, succinate, fumarate, malate, oxaloacetate, and derivatives thereof, including but not limited to isomers and acids. In a particular embodiment, low sugar media comprises two or more tricarboxylic acid cycle intermediates, including but not limited to, pyruvate, acetyl-CoA, citrate, isocitrate, $\alpha$-ketoglutarate, succinyl-CoA, succinate, fumarate, malate, oxaloacetate, and derivatives thereof, including but not limited to isomers and acids.

Certain embodiments of the invention utilize concentrations of a tricarboxylic acid cycle intermediate selected from the following ranges: 0.01 to 5.0 mg/ml; 0.01 to 0.25 mg/ml; 0.01 to 0.5 mg/ml; 0.01 to 1 mg/ml; 0.01 to 2.5 mg/ml; 0.01 to 5 mg/ml; 0.05 to 0.1 mg/ml; 0.05 to 1.0 mg/ml; 0.05 to 2.5 mg/ml; 0.1 to 0.25 mg/ml; 0.1 to 0.5 mg/ml; 0.1 to 1 mg/ml; 0.1 to 2.5 mg/ml; 0.1 to 5 mg/ml; 0.15 to 0.45 mg/ml; 0.15 to 0.5 mg/ml; 0.25 to 0.35 mg/ml; 0.25 to 0.5 mg/ml; 0.25 to 1 mg/ml; 0.25 to 2.5 mg/ml; 0.25 to 5 mg/ml; 0.35 to 0.5 mg/ml; 0.35 to 1 mg/ml; 0.35 to 2.5 mg/ml; 0.35 to 5 mg/ml; 0.5 to 1 mg/ml; 0.5 to 2.5 mg/ml; 0.5 to 5 mg/ml; 1 to 2.5 mg/ml; 1 to 5 mg/ml; about 0.05 mg/ml; about 0.1 mg/ml; about 0.15 mg/ml; about 0.25 mg/ml; about 0.35 mg/ml; about 0.45 mg/ml; and about 0.5 mg/ml.

In other embodiments, low sugar media may comprise one or more cryoprotectants, including but not limited to, propylene glycol, dimethyl sulfoxide, ethylene glycol and glycerol, or a combination thereof. In certain embodiments, low sugar media may comprise a concentration of cryoprotectant by percent volume selected from the following: less than 1%; 1-5%; 5%; 5 to 10%; 10%; 10 to 20%; 16.7%; 20%; 20 to 30%; or 30 to 40%.

In a further embodiment, low sugar media may comprise one or more antioxidants, including but not limited to catalase, superoxide dismutase (SOD), SOD mimics, glutathione, glutathione reductase, glutathione peroxidase, pyruvate, mercaptoethanol, butylatedhydroxytoluene (BHT), lipoic acid, flavonoids, phenolic acids and their esters, quinines, vitamin A (and related vitamers), vitamin C (and related vitamers), vitamin K (and related vitamers), vitamin B12 (and related vitamers), with "vitamers" defined as compounds having the same vitamin activity (such as cobalamin, cyanocobalamin, methylcobalamin, adenosylcobalamin, hydroxocobalamin, and pseudo-B12), vitamin E (including its vitamers, tocopherols ($\alpha$, $\beta$, $\gamma$), tocotrienols, and $\alpha$-tocopheryl), $\alpha$-ketoglutarate (also known as $\alpha$-KG, AKG or oxo-glutarate) and various biological forms of AKG (such as arginine, aspartate, lysine, and similar derivatives), coenzyme Q, manganese, iodide, melatonin and carotenoid terpenoids.

Certain embodiments of the invention utilize concentrations of an antioxidant selected from the following ranges: 0.01 to 5.0 mg/ml; 0.01 to 0.25 mg/ml; 0.01 to 0.5 mg/ml; 0.01 to 1 mg/ml; 0.01 to 2.5 mg/ml; 0.01 to 5 mg/ml; 0.05 to 0.1 mg/ml; 0.05 to 1.0 mg/ml; 0.05 to 2.5 mg/ml; 0.1 to 0.25 mg/ml; 0.1 to 0.5 mg/ml; 0.1 to 1 mg/ml; 0.1 to 2.5 mg/ml; 0.1 to 5 mg/ml; 0.15 to 0.45 mg/ml; 0.15 to 0.5 mg/ml; 0.25 to 0.35 mg/ml; 0.25 to 0.5 mg/ml; 0.25 to 1 mg/ml; 0.25 to 2.5 mg/ml; 0.25 to 5 mg/ml; 0.35 to 0.5 mg/ml; 0.35 to 1 mg/ml; 0.35 to 2.5 mg/ml; 0.35 to 5 mg/ml; 0.5 to 1 mg/ml; 0.5 to 2.5 mg/ml; 0.5 to 5 mg/ml; 1 to 2.5 mg/ml; 1 to 5 mg/ml; about 0.05 mg/ml; about 0.1 mg/ml; about 0.15 mg/ml; about 0.25 mg/ml; about 0.35 mg/ml; about 0.45 mg/ml; and about 0.5 mg/ml.

In yet another embodiment, low sugar media may comprise one or more protein sources, including but not limited to, egg yolk, egg yolk extract, milk (including heat homogenized and skim), milk extract, soy protein, soy protein extract, serum albumin, bovine serum albumin, human serum substitute supplement, seminal proteins, such as, for example, whole seminal plasma or seminal plasma extracts, and derivatives thereof. In certain embodiments, low sugar media may comprise a concentration of protein source by percent volume selected from the following: 1-5%; 5%; 5 to 10%; 10%; 10 to 20%; 16.7%; 20%; 20 to 30%; or 30 to 40%.

In a further embodiment of the invention, low sugar media may comprise one or more antimicrobial or antibiotic agents, including but not limited to, tylosin, gentamicin, lincomycin, spectinomycin, Linco-Spectin® (lincomycin hydrochloride-spectinomycin), penicillin, streptomycin, ticarcillin, polymyxin B, and their derivatives. If included, the antibiotics may be present in a concentration of about 50

μg to about 800 μg per ml of semen. In another embodiment low sugar media may comprise a detergent, including but not limited to, an alkyl ionic detergent such as sodiumdodecyl sulfate (SDS).

In another embodiment, low sugar media may comprise one or more salts, including but not limited to, NaCl, KCl, $MgCl_2$, $CaCl_2$) and any combination of a salt-forming anion, including but not limited to acetate ($CH_3COO^-$), carbonate ($CO_3^{2-}$), chloride ($Cl^-$), citrate ($HOC(COO^-)(CH2COO^-)_2$), fluoride ($F^-$), nitrate ($NO_3^-$), nitrite ($NO_2^-$), phosphate ($PO_4^{3-}$) and sulfate ($SO_4^{2-}$) and a salt-forming cation, including but not limited to, ammonium ($NH_4^+$), calcium ($Ca^{2+}$), iron ($Fe^{2+}$ and $Fe^{3+}$), magnesium ($Mg^{2+}$), potassium ($K^+$), pyridinium ($C_5H_5NH^+$), quaternary ammonium $NR_4^+$ and sodium ($Na^+$).

In yet another embodiment, low sugar media may comprise one or more growth factors including but not limited to transforming growth factors ("TGF"), such as, for example, TGFβ-1 and TGFβ-2, and insulin-like growth factors ("IGF"), such as for example, IGF-1.

Another embodiment of the invention encompasses a staining solution comprising low sugar media and a DNA selective dye. DNA selective dyes for use with the invention include but are not limited to UV light excitable, selective dyes, such as Hoechst 33342 and Hoechst 33258 and visible light excitable dyes, such as SYBR-14 and bisbenzimide-BODIPY® conjugate 6-{[3-((2Z)-2-{[1-(difluoroboryl)-3,5-dimethyl-1H-pyrrol-2yl]methylene}-2H-pyrrol-5-yl)propanoyl]amino}-N-[3-(methyl{3-[({4-[6-(4-methylpiperazin-1-yl)-1H,3'H-2,5'bibenzimidazol-2'-yl]phenoxy}acetypamino]propyl}amino)propyl]hexanamide. Each of these dyes may be used alone or in combination. In another embodiment, the staining solution further comprises one or more dye quenchers, including but not limited to F&DC red food dye No. 40 and yellow food dye No. 4. In yet another embodiment, the staining solution further comprises one or more OSRs.

In one embodiment of the invention, the concentration of dye in the staining solution is from about 0.1 μM to about 1.0M; from about 0.1 μM to about 1000 μM; from about 100 μM to about 500 μM; from about 200 μM to about 500 μM; from about 300 μM to about 450 μM; about 350 μM; about 400 μM; or about 450 μM.

The pH of low sugar media of the invention may be maintained at any of a range of pHs suitable for the particular process and sperm type. In certain embodiments, this will be in the range of about 5.0 to about 9.0; in the range of 5.5 to 7.8; from about 5.0 to about 7.0; from about 6.0 to about 7.0; from about 6.0 to about 6.5; about 6.2, about 6.5; about 6.6; about 6.7; about 6.8; about 6.9; or about 7.0; from about 7.0 to about 9.0; from about 7.0 to about 8.0; from about 7.0 to about 7.5; about 7.0; about 7.1; about 7.2; about 7.3; about 7.35; about 7.4; or about 7.5.

In certain embodiments, low sugar media may be combined with a sperm sample to form a sperm composition. The term "sperm sample" may comprise a processed semen sample or an unsorted, conventional semen sample. In some embodiments of the invention, the sperm composition comprising low sugar media is used with ART. Such ART techniques involve different levels of gamete cell processing which in the case of sperm can entail, by example only and is not limited to one or more of the following: artificially collecting a semen sample from the male animal that may involve natural, electronic or other types of sexual stimulation; holding; transporting; buffering with different pHs; chilling; warming; staining; diluting; concentrating; energetically exciting as with a laser; electronic charging; deflecting; ablating to kill unwanted cells usually with targeted lasers; sorting; collecting; shaking; oscillating; magnetically separating; oxygenating as associated with microchip sorting procedures; labeling; precipitating; centrifuging; resuspending; mixing; dialyzing; cryostabilizing; freezing; vitrifying; cryopreserving; thawing; culturing; inseminating; microinjecting; microfluidic processing; microchip processing; jet and air processing; flow cytometry processing; and similar handling techniques. Whereas a single processing step may exert only minimal stress on a sperm, others or a combination may add significant stress, often killing the cell. An example is the sex sorting process used to separate X- from Y-chromosome bearing cells; the sorting process combines a large number of independent stressful steps that compromise the overall integrity of the sorted sperm population.

In some embodiments of the invention, a sperm composition comprising a sperm sample and low sugar media can be used immediately or processed within the first few minutes after the sperm sample is added to the low sugar media for whatever processing step is needed, whereby the holding period would be in the range 2 sec to 3 min. In other embodiments, holding periods can be short, as in the range of a 3-15 minutes, moderate as in the range of 15 min to 1 hr; and longer processing periods ranging up to about 8 hrs or overnight for extensive processing such as with sex sorting techniques. Transportation hold periods associated with transporting unfrozen sperm compositions can be much longer, extending up to a few days, which may for example occur if the sperm sample is collected, added to the low sugar media, transported or shipped to another location possibly by air, and further processed at the second location as for sex sorting at a designated facility. In other instances, the sperm composition might need to be held for a few days while a recipient female is hormonally prepped for artificial insemination, as might occur if a sample is mistakenly thawed and cannot be refrozen. The use of low sugar media could theoretically prolong these extended hold periods over what is currently accepted in the art, and could provide sufficient protection to the sperm in the sperm composition so that they could remain viable and fertile for up to a week or more.

In some embodiments of the invention, low sugar media is used several times during a complex processing procedure to minimize cell stress throughout the procedure. In other embodiments, low sugar media is used only at one or more particular steps which are notably harsh on the cells to help minimize stress and fatigue on the sperm. By way of example, the staining process during sex sorting is often performed at non-physiological pH and at elevated temperatures, both known to be harsh on the cells. Similarly, cryopreservation is also extremely harsh on the cells and disrupts cell membranes, both internal and external. Following an intensive multi-step sorting procedure, sex sorted sperm which are already compromised are even more susceptible to cryogenic and freeze processing.

A further embodiment of the present invention provides a method of improving the motility, viability and/or fertility of a sperm sample that has already undergone a sorting process, including but not limited to sex sorting, comprising the step of contacting or adding a sorted sperm sample to low sugar media that may also comprise at least one OSR in the concentration range of 0.01 mg/ml to 5 mg/ml to form a sperm composition.

Another broad object of the present invention is to improve the motility, viability (including longevity and ability to survive environmental stress) and fertility of processed and/or sorted sperm for use in ART such as IVF, AI, ICSI (as well as other techniques using enucleated cells), and MOET (as well as other embryo transfer techniques). Some embodiments of the invention encompass low sugar media comprising a sorted or processed sperm sample, and optionally at least one OSR in the range of 0.01 mg/ml to 5 mg/ml, for use in ART. An additional embodiment of the invention encompasses a frozen or vitrified sperm composition comprising low sugar media, a processed or sorted sperm sample, and optionally, at least one OSR in the concentration range of 0.01 mg/ml to 5 mg/ml.

A further embodiment of the invention resides in a method of making an embryo comprising mixing at least one egg with at least one sperm contacted with low sugar media, which may also comprise at least one OSR in the concentration range of 0.01 mg/ml to 5 mg/ml. The embryos produced by this method constitute a further embodiment of the invention.

Another embodiment of the invention includes a method for inseminating an organism through an AI technique using a processed or sorted sperm sample contacted with low sugar media that may also comprise at least one OSR in the concentration of 0.01 mg/ml to 5 mg/ml. The progeny of the organism that results from the aforementioned AI method also constitutes an embodiment of the invention. A further embodiment of the invention encompasses a method for recovering embryos that are produced from the aforementioned AI method.

Embodiments of the invention can include sperm, or spermatozoa, collected from numerous species of male animals, and the invention should be understood not to be limited to the species of male animals described by the specific examples within this application. Rather the specific examples within this application are intended to be illustrative of the varied and numerous species of male animals from which semen can be collected and utilized in certain embodiments of the invention. Embodiments of the invention, for example, may include the sperm of humans as well as animals having commercial value for meat or dairy production such as swine, ovine, bovine, equine, deer, elk, buffalo, or the like (naturally the mammals used for meat or dairy production may vary from culture to culture). It may also include the sperm of various domesticated mammalian species encompassed by canines and felines, as well as sperm of primates, including but not limited to chimpanzees, gorillas, or humans and the spermatozoa from whales, dolphins and other marine mammals. It may also include frozen-thawed sperm from all the various mammals above-described and further, including but not limited to, the sperm of deceased donors, from rare or exotic mammals, zoological specimens, or endangered species.

A particular embodiment of the invention comprises a method of sorting a sperm sample to form one or more subpopulations comprising the steps of providing a sperm sample, sorting the sperm sample to form one or more subpopulations and using a low sugar media during one or more of the aforementioned sorting steps. In the context of sorting sperm using a flow cytometer, for example, low sugar media may be used in a diluent for diluting sperm, a staining solution for staining the sperm with, for example, a DNA selective dye, a sheath fluid for encapsulating the core stream containing the sperm as it passes through the flow cytometer, a catch media for receiving one or more of the sorted sperm subpopulations, or a resuspension media for resuspending processed sperm.

Another embodiment of the invention encompasses a method of sorting sperm comprising staining the sperm with a staining solution; sorting the sperm using a flow cytometer with a sheath fluid into one or more subpopulations, wherein at least 60% of sperm in one of the one or more subpopulations bear X chromosomes or bear Y chromosomes; and collecting the one of the one or more subpopulations in a catch media; wherein the staining solution, the sheath fluid or the catch media is low sugar and may further comprise one or more OSRs. In a certain embodiment of the invention, any combination of the staining solution, the sheath fluid and the catch media may be sugar free and comprise one or more OSRs. In further embodiments, the one or more OSRs may be different or identical between the staining solution, the sheath fluid and the catch media, and in other embodiments, the one or more OSRs may be identical between the staining solution, the sheath fluid and the catch media. In a further embodiment, a diluent or resuspension media used for processing the sperm is also sugar free and may also comprises one or more OSRs. In a yet further embodiment, the staining solution, the sheath fluid or the catch media is low sugar and comprises a buffer, a chelator and a plurality tricarboxylic acid cycle intermediates.

In another embodiment of the invention, low sugar media, including but not limited to diluents, staining solutions, sheath fluids, catch media, and resuspension media, shifts sperm metabolism away from glycolytic metabolism and towards tricarboxylic acid cycle metabolism.

The invention also encompasses a method of processing sperm comprising contacting the sperm with low sugar media comprising a cryoprotectant and optionally, one more OSRs, wherein the low sugar media comprising the cryoprotectant has been frozen and thawed prior to contacting with the sperm. A further embodiment of the inventions encompasses low sugar media comprising a cryoprotectant, wherein the low sugar media comprising the cryoprotectant has been frozen and thawed prior to addition of the sperm. An additional embodiment of the invention encompasses low sugar media used in processing sperm that comprises at least one antioxidant and/or OSR at the appropriate stock concentration to be present at a final processing concentration in the range of 0.01 mg/ml to 5 mg/ml in the sperm composition at the time of processing. In some embodiments, low sugar media can be used for different processes including but not limited to sperm collection, artificial insemination, sperm sorting, in vitro fertilization, embryo culture, as well as sperm and embryo freezing. In particular embodiments, low sugar media used in the sorting of sperm typically comprises one or more buffers and/or extenders (i.e., substances that preserve the viability and/or fertility of sperm).

In another embodiment, the invention encompasses low sugar media that is cell-free and comprises a cryoprotectant, wherein the low sugar media has been frozen and then thawed. In a further embodiment, the low sugar media may also comprise one or more OSRs. For purposes of the aforementioned embodiments, the term "cell-free" means the media is free of cells collected from a subject (e.g., sperm and blood cells), processed cells and laboratory grown or cultured cells.

In a further embodiment, the invention encompasses a method of processing sperm comprising the steps of forming a stream comprising sperm and a first media; determining a property of said sperm in said stream; selecting sperm having a property of interest from said sperm in said stream; and collecting said sperm having said property of interest in a second media, wherein the first or second media comprise low sugar media. In certain, embodiments, the property of interest may be the presence of an X or Y chromosome. In a further embodiment, the first and second media are identical in terms of their components and relative concentrations of those components. In another embodiment, the first and second media are different in terms of their components and/or relative concentrations of those components. In yet another embodiment, the step of selecting sperm having a property of interest from said sperm in said stream comprises photo-damaging said sperm having said property of interest or isolating said sperm having said property of interest. In yet another embodiment, the aforementioned method further comprises the step of resuspending the sperm having the property of interest (after, for example, a cell concentrating step or centrifugation) in a third media comprising low sugar media.

In another embodiment, the invention encompasses a method of processing sperm comprising freezing and thawing a media comprising low sugar media and a protein source; and contacting sperm with the media. In a particular embodiment, the protein source comprises egg yolk.

An additional embodiment of the invention encompasses a composition comprising sperm and low sugar media and a protein source, wherein the media has been frozen and thawed prior to addition of the sperm. In yet a further embodiment, the protein source comprises egg yolk.

Another embodiment of the invention encompasses a composition comprising a gender enriched sperm population and low sugar media. In a further embodiment, the composition further comprises a protein source, such as egg yolk.

BRIEF DESCRIPTION OF THE DRAWINGS

In order that the invention may be more clearly understood, various embodiments of the present invention will now be described by way of example only with reference to the accompanying sheets of drawings wherein.

DETAILED DESCRIPTION OF THE INVENTION

Figure 1:
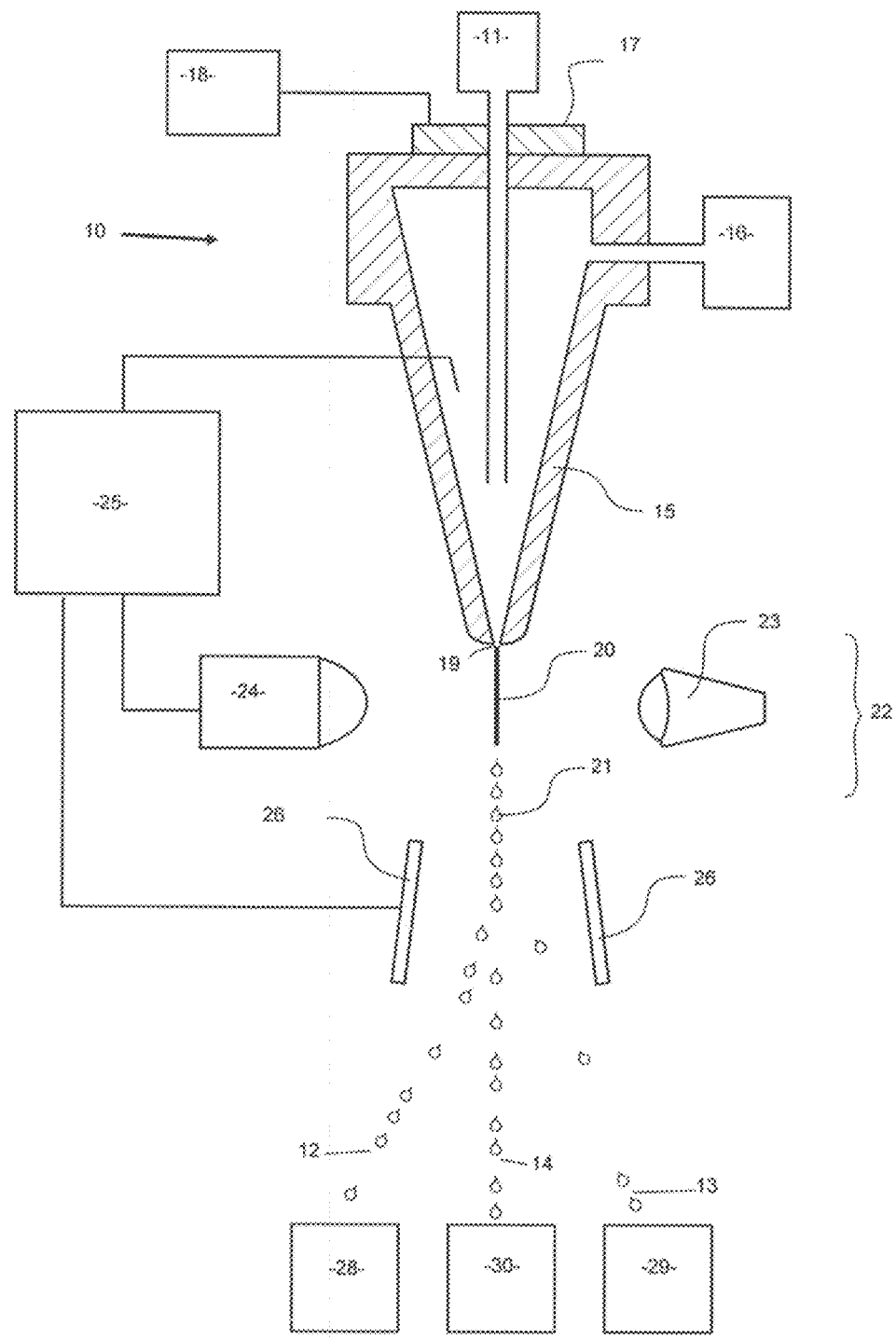
FIG. 1 is a schematic representation of part of a flow cytometer illustrating a method of sorting a sperm sample into one or more subpopulations according to some embodiments of the present invention.
Figure 2:
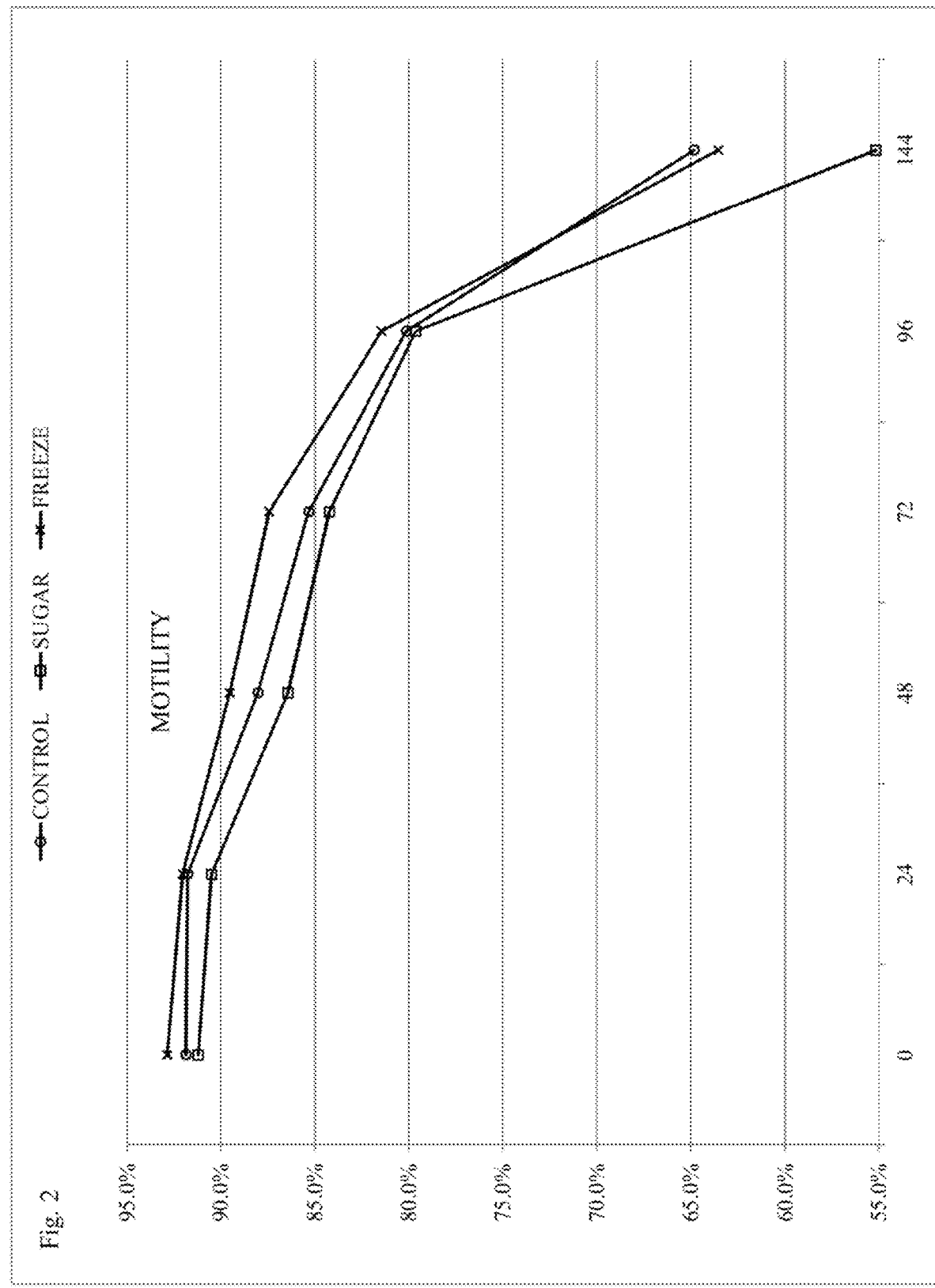
FIG. 2 is a graphical depiction of the post-sort sperm motility of different treatment groups in Example 1 over time.
Figure 3:
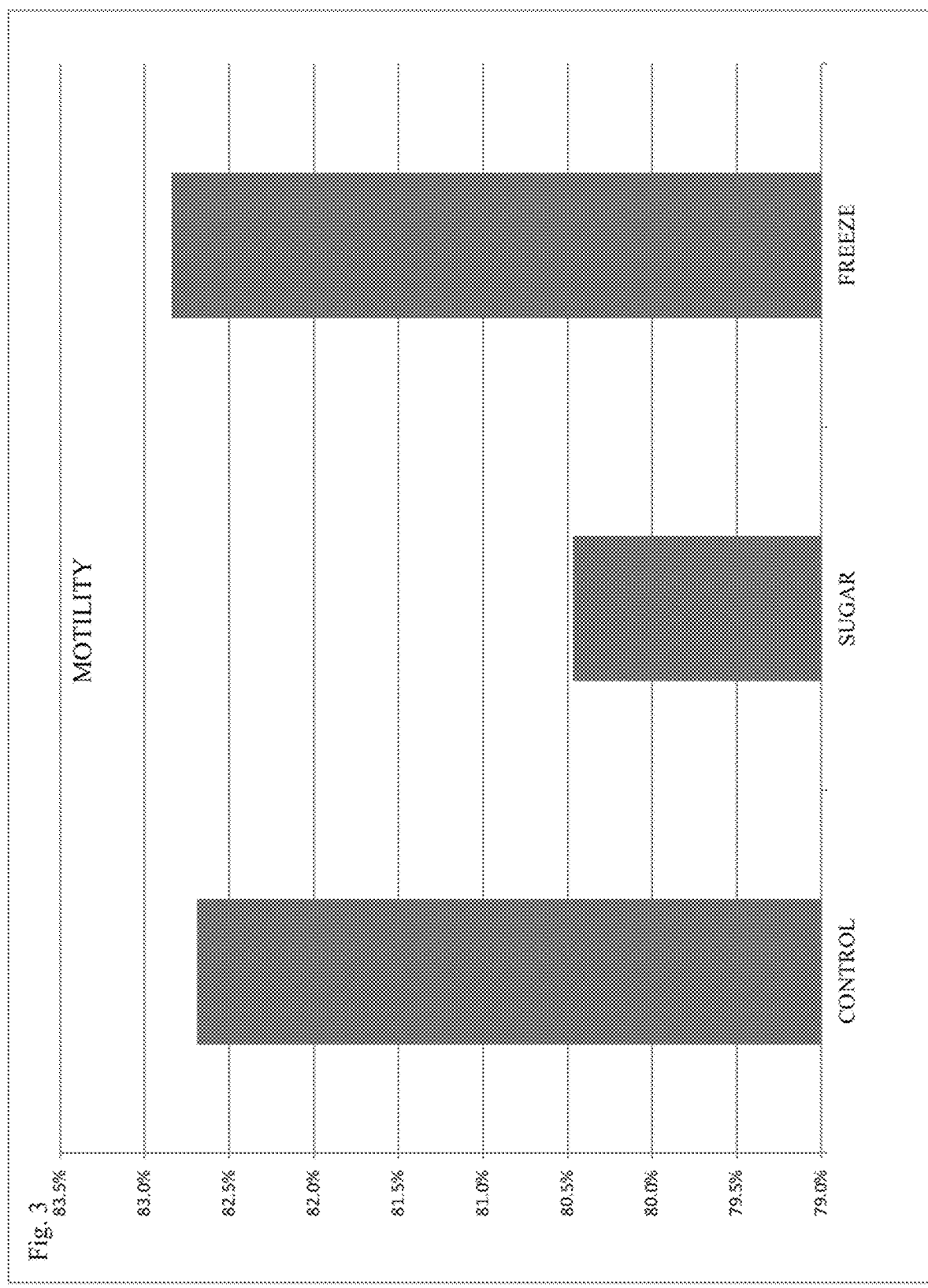
FIG. 3 is a graphical depiction of the post-sort sperm motility of different treatment groups in Example 1.
Figure 4:
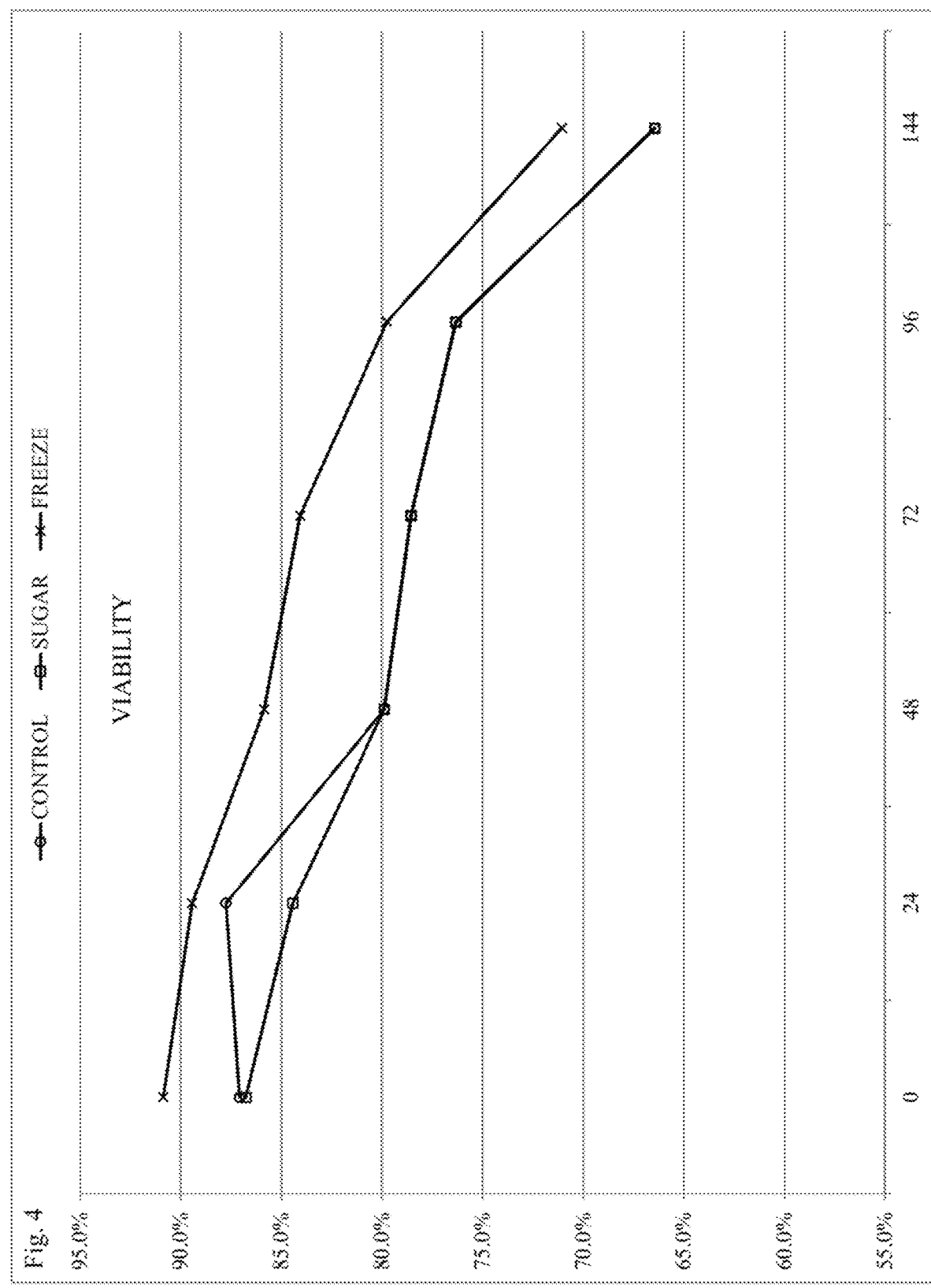
FIG. 4 is a graphical depiction of the post-sort sperm viability of different treatment groups in Example 1 over time.
Figure 5:
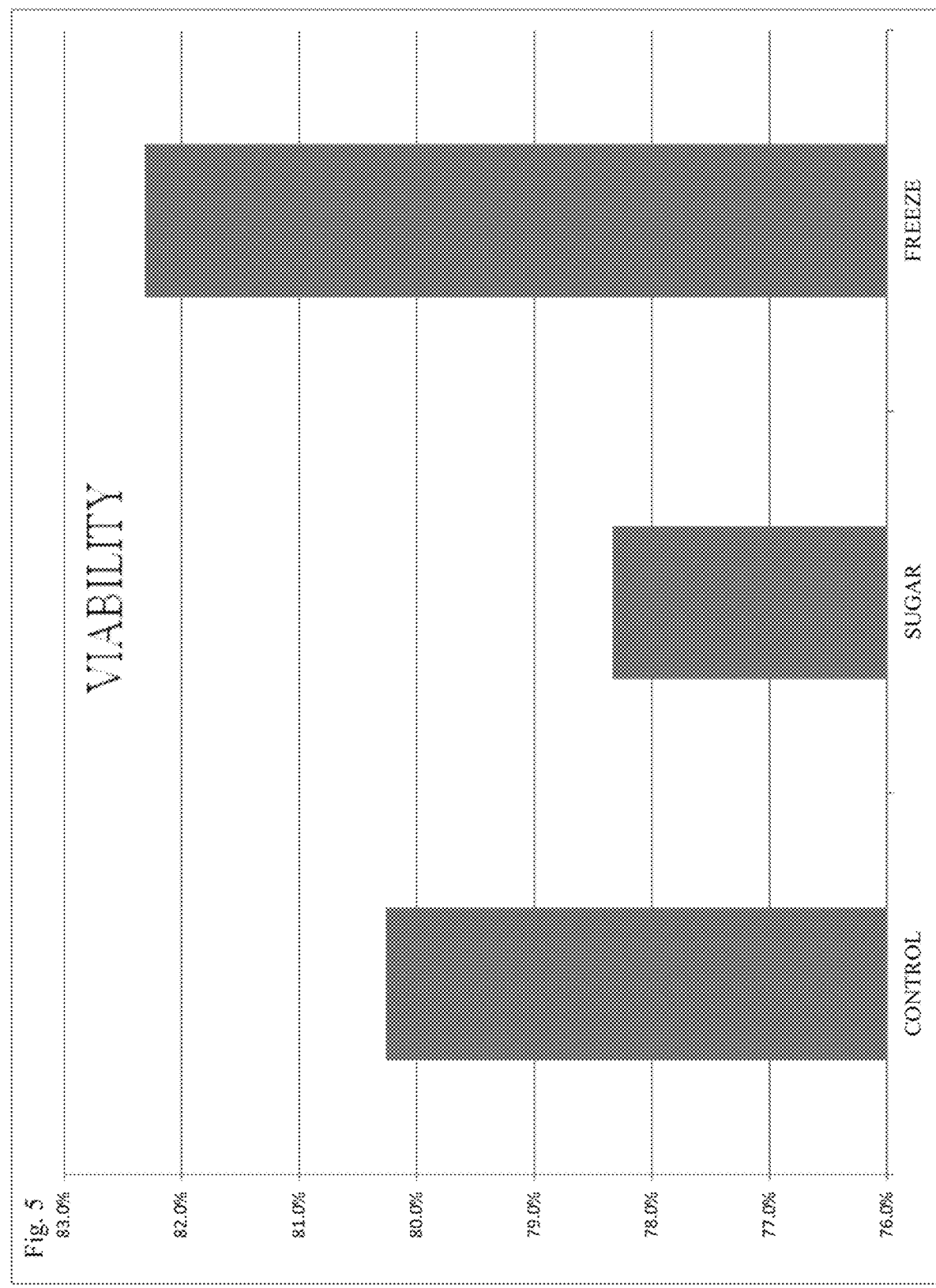
FIG. 5 is a graphical depiction of the post-sort sperm viability of different treatment groups in Example 1.
Figure 6:
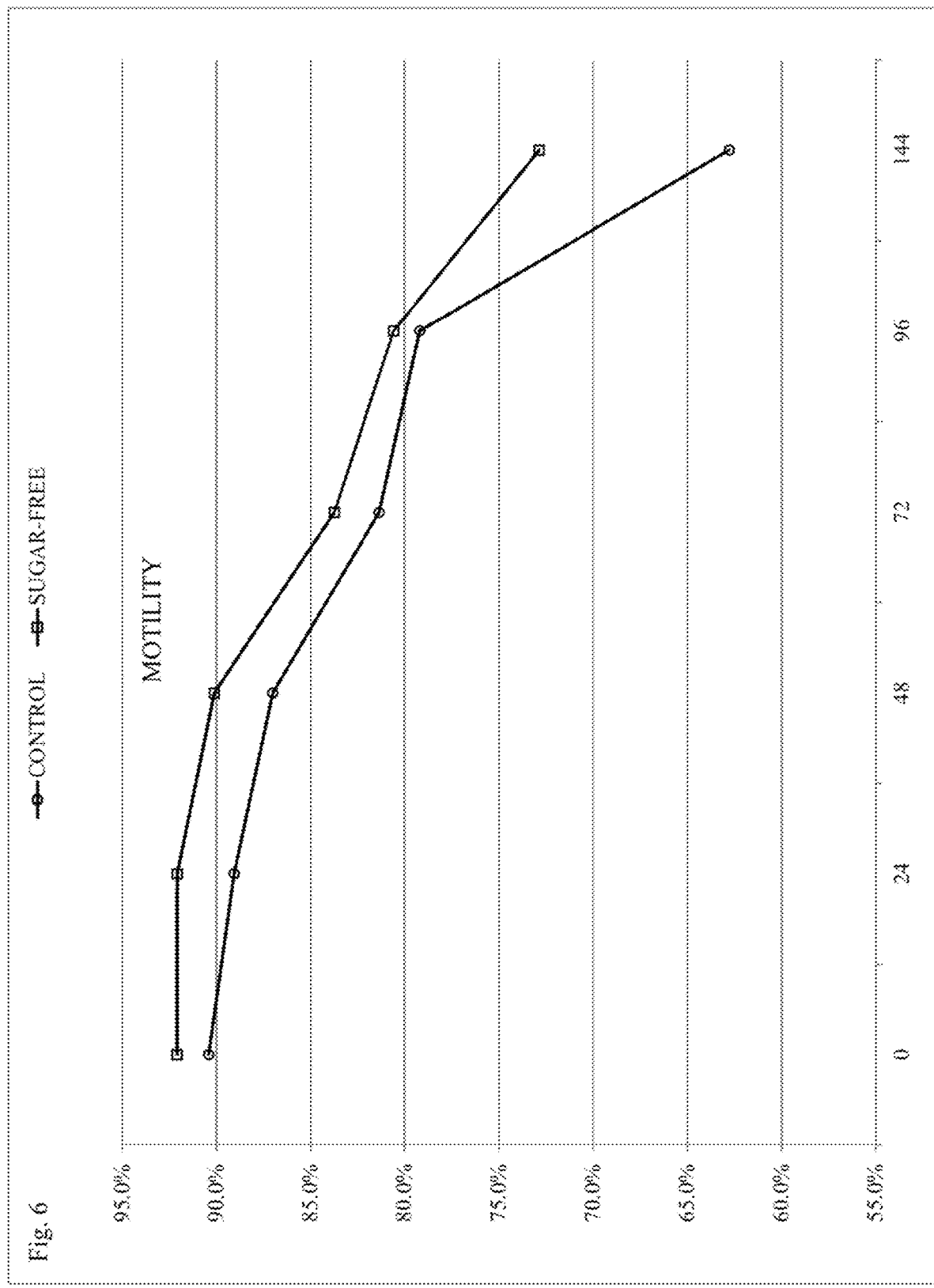
FIG. 6 is a graphical depiction of the post-sort sperm motility of different treatment groups in Example 2 over time.
Figure 7:
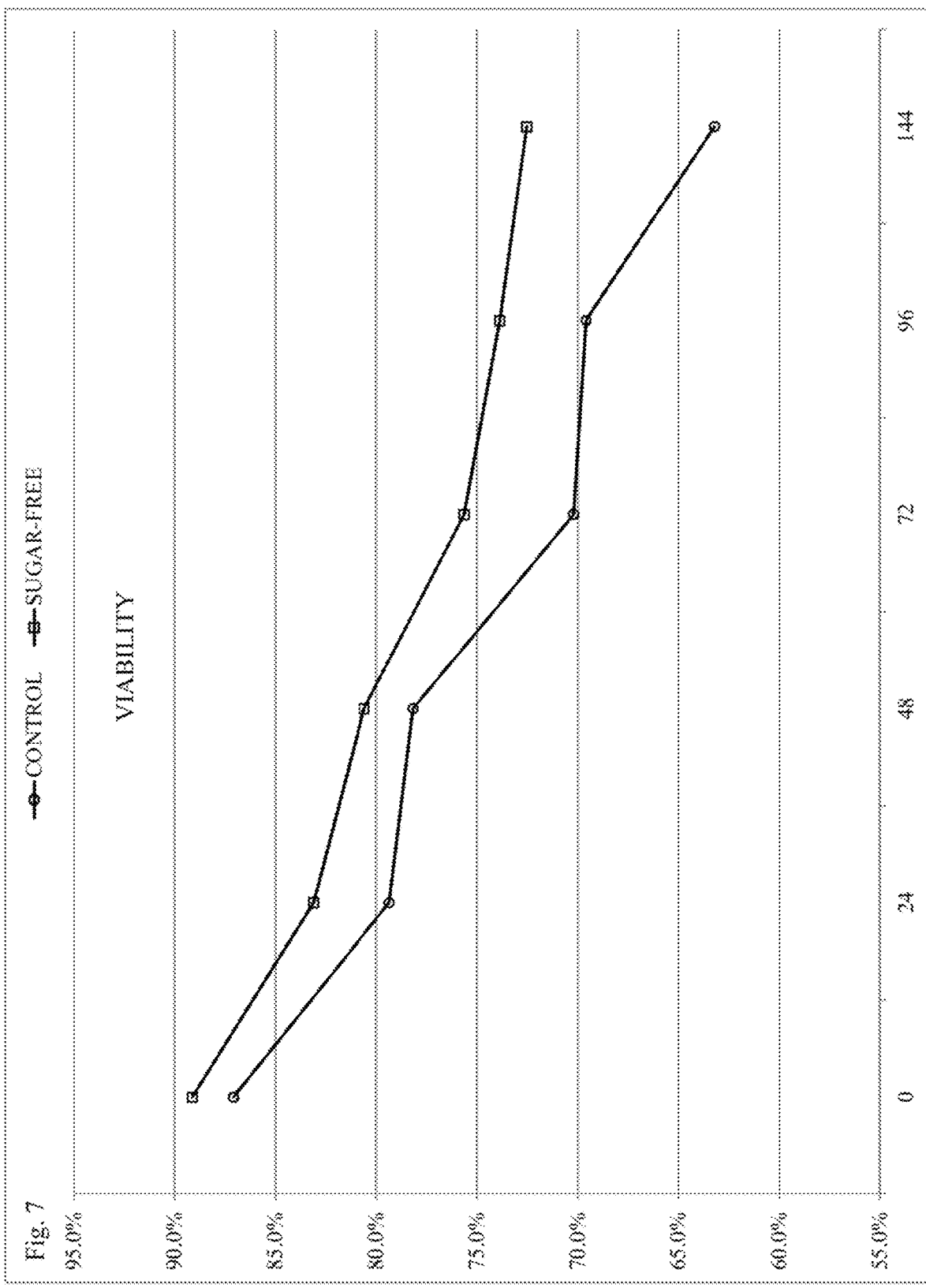
FIG. 7 is a graphical depiction of the post-sort sperm viability of different treatment groups in Example 2 over time.
Figure 8:
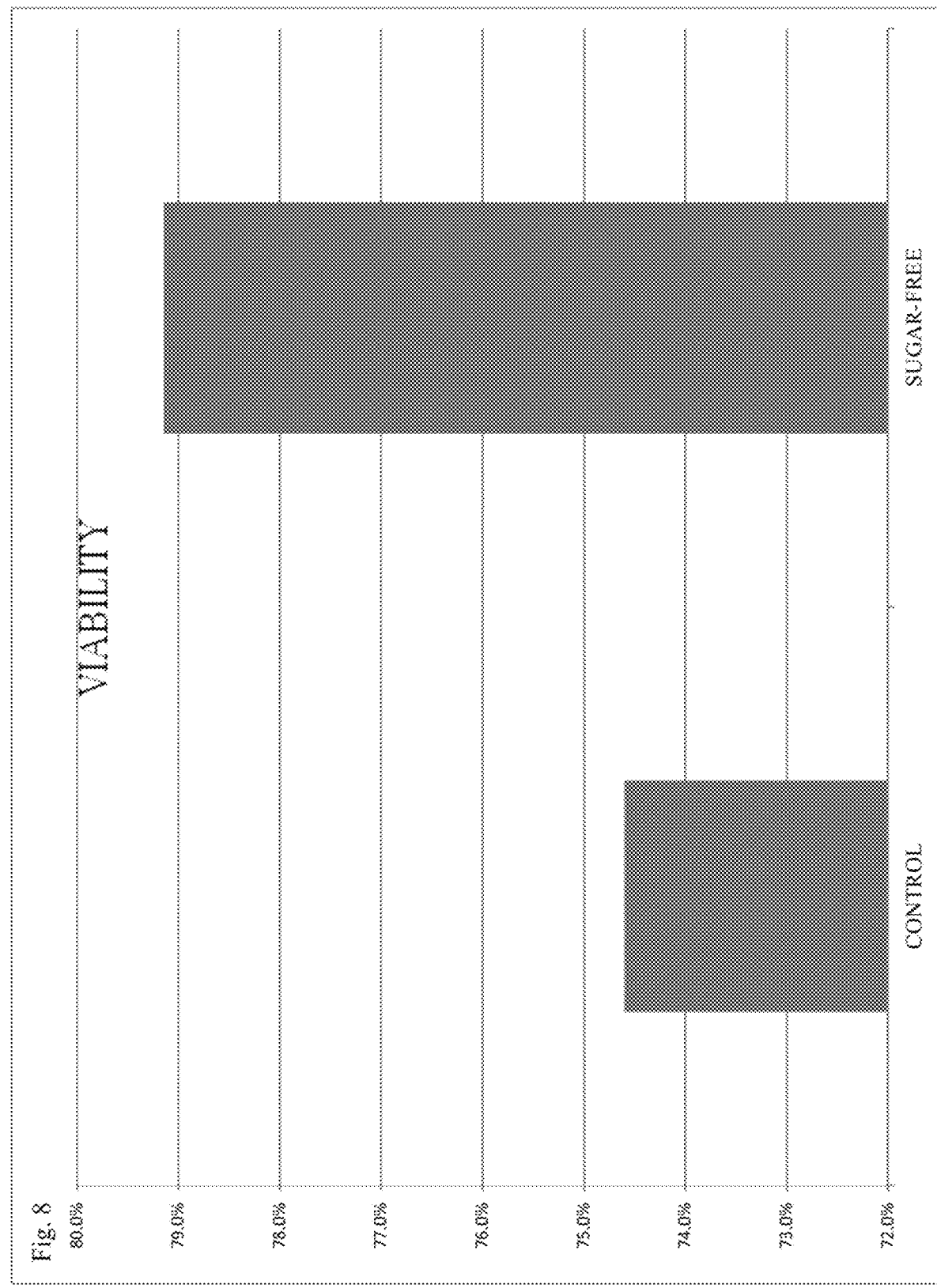
FIG. 8 is a graphical depiction of the post-sort sperm viability of different treatment groups in Example 2.
Figure 9:
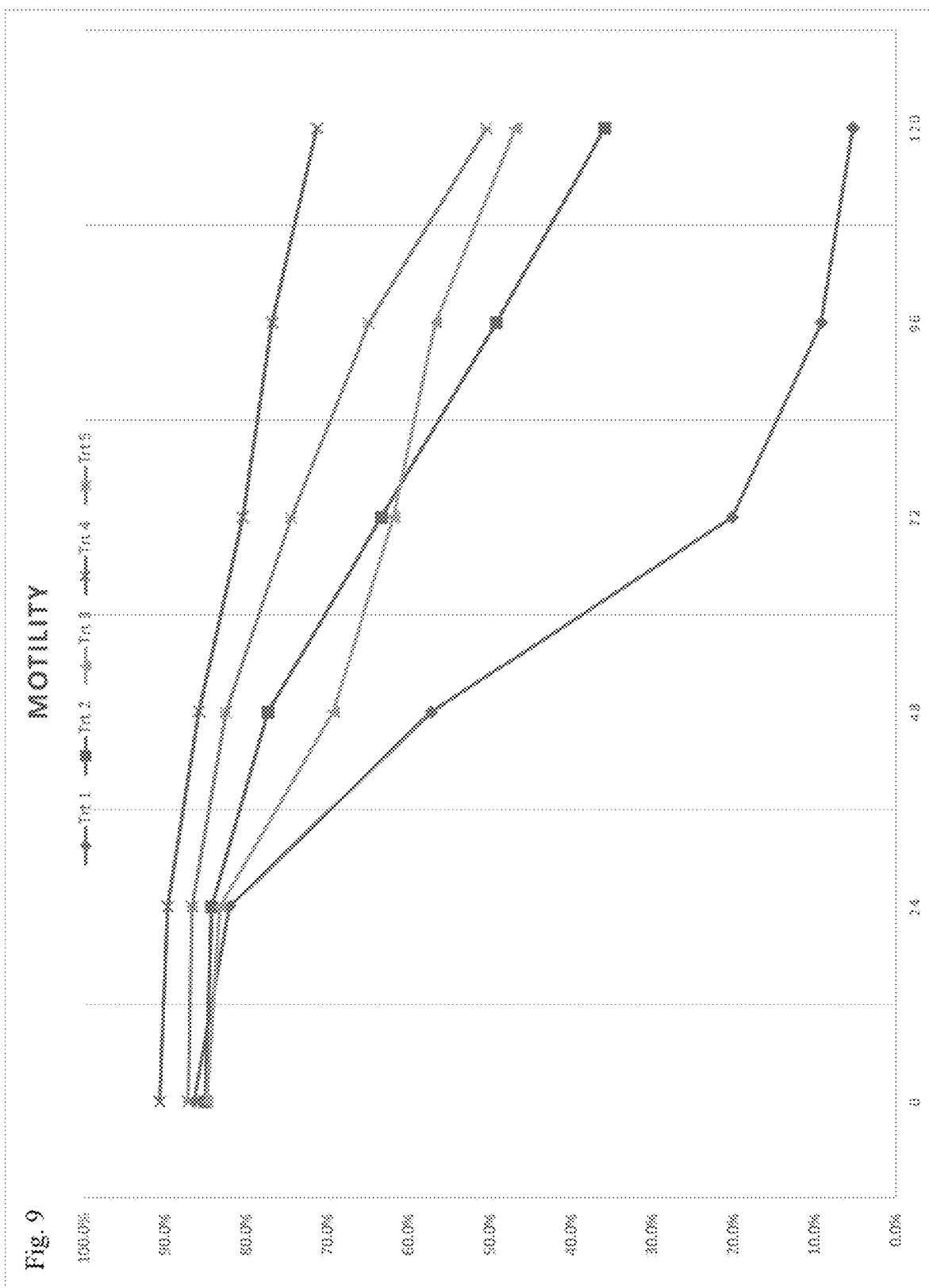
FIG. 9 is a graphical depiction of the post-sort sperm motility of different treatment groups in Example 3 over time.
Figure 10:
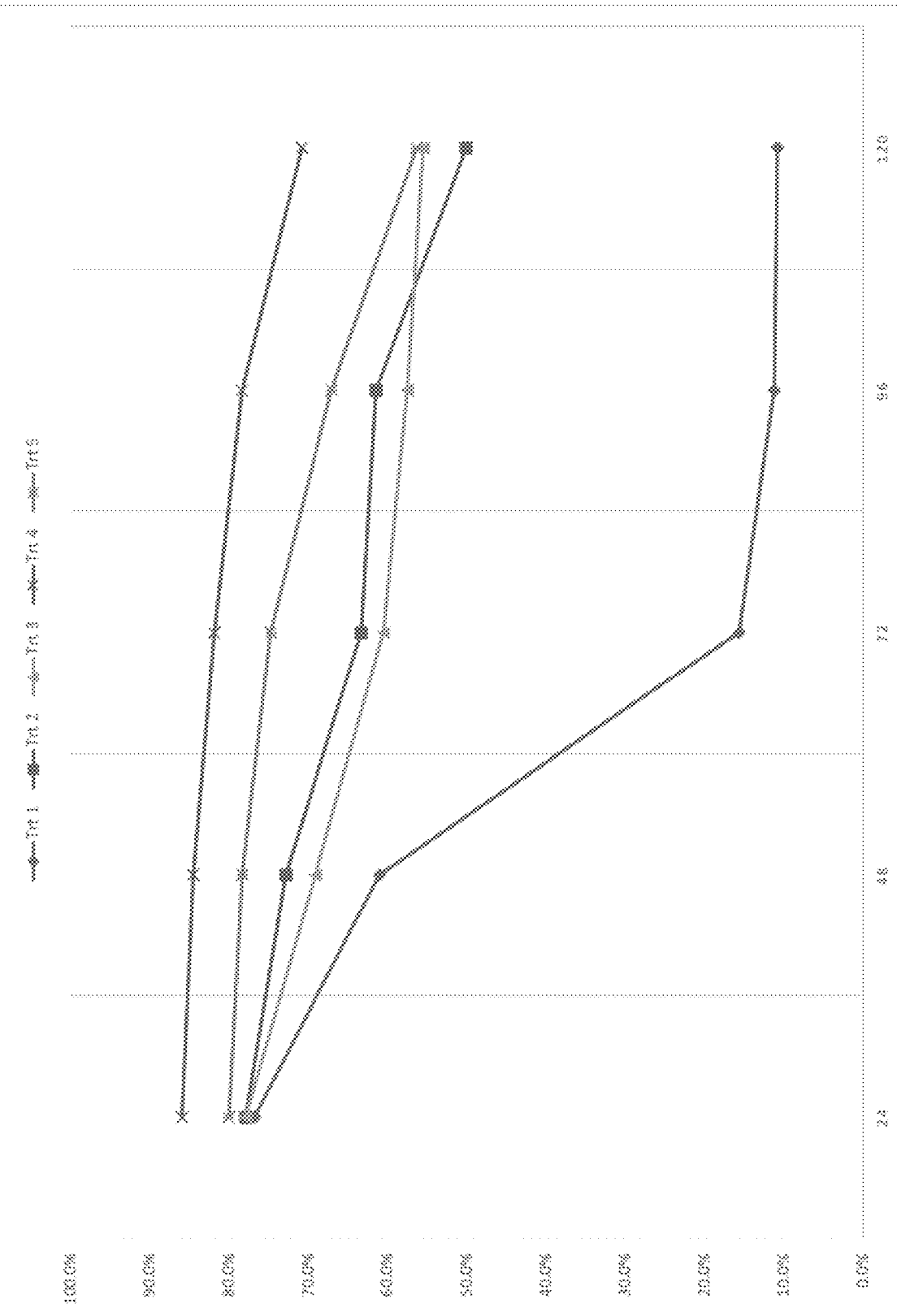
FIG. 10 is a graphical depiction of the post-sort sperm viability of different treatment groups in Example 3 over time.
Figure 11:
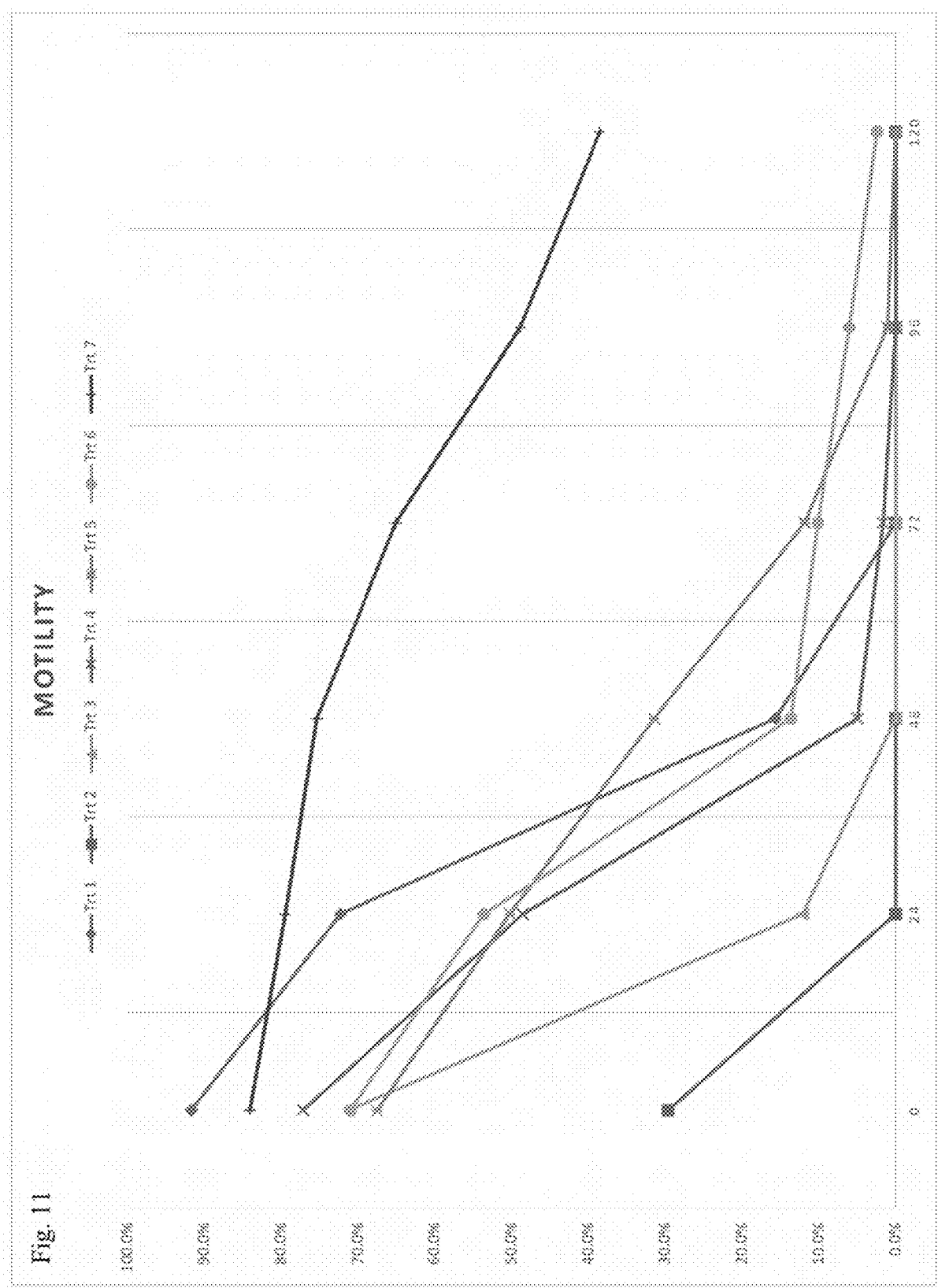
FIG. 11 is a graphical depiction of the post-sort sperm motility of different treatment groups in Example 4 over time.
Figure 12:
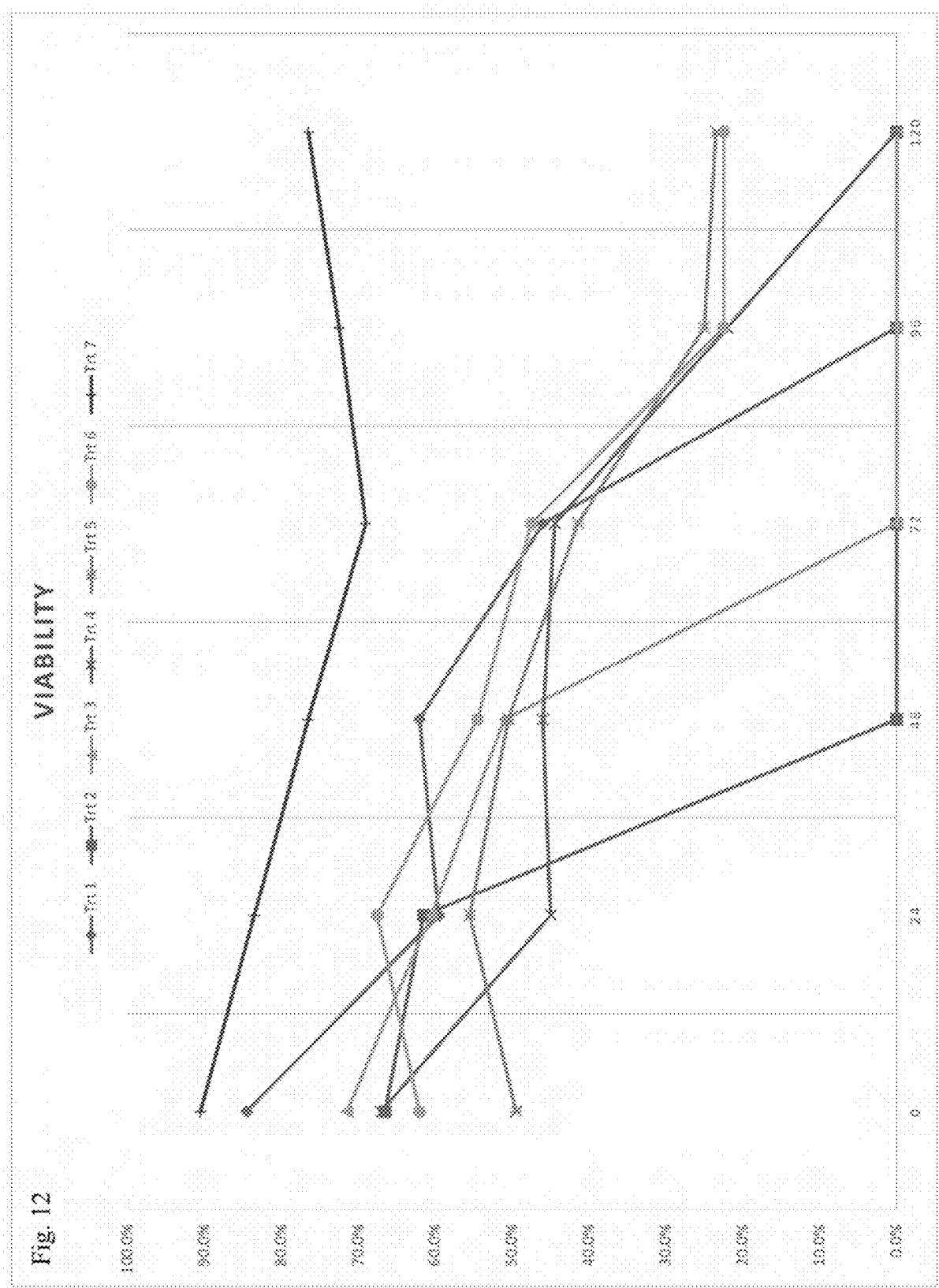
FIG. 12 is a graphical depiction of the post-sort sperm viability of different treatment groups in Example 4 over time.
Figure 13:
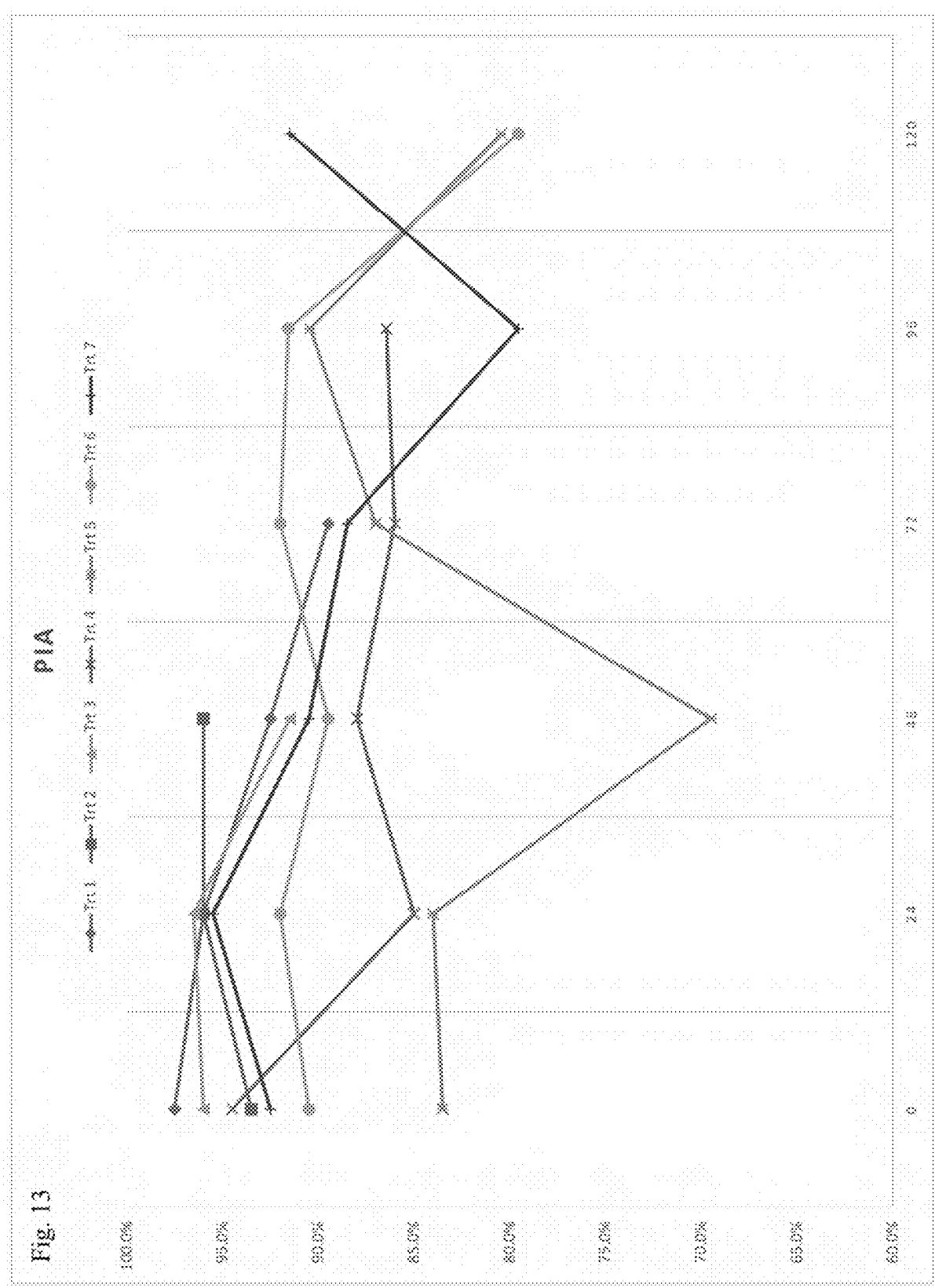
FIG. 13 is a graphical depiction of the percent intact acrosomes of different treatment groups in Example 4 over time.
Figure 14:
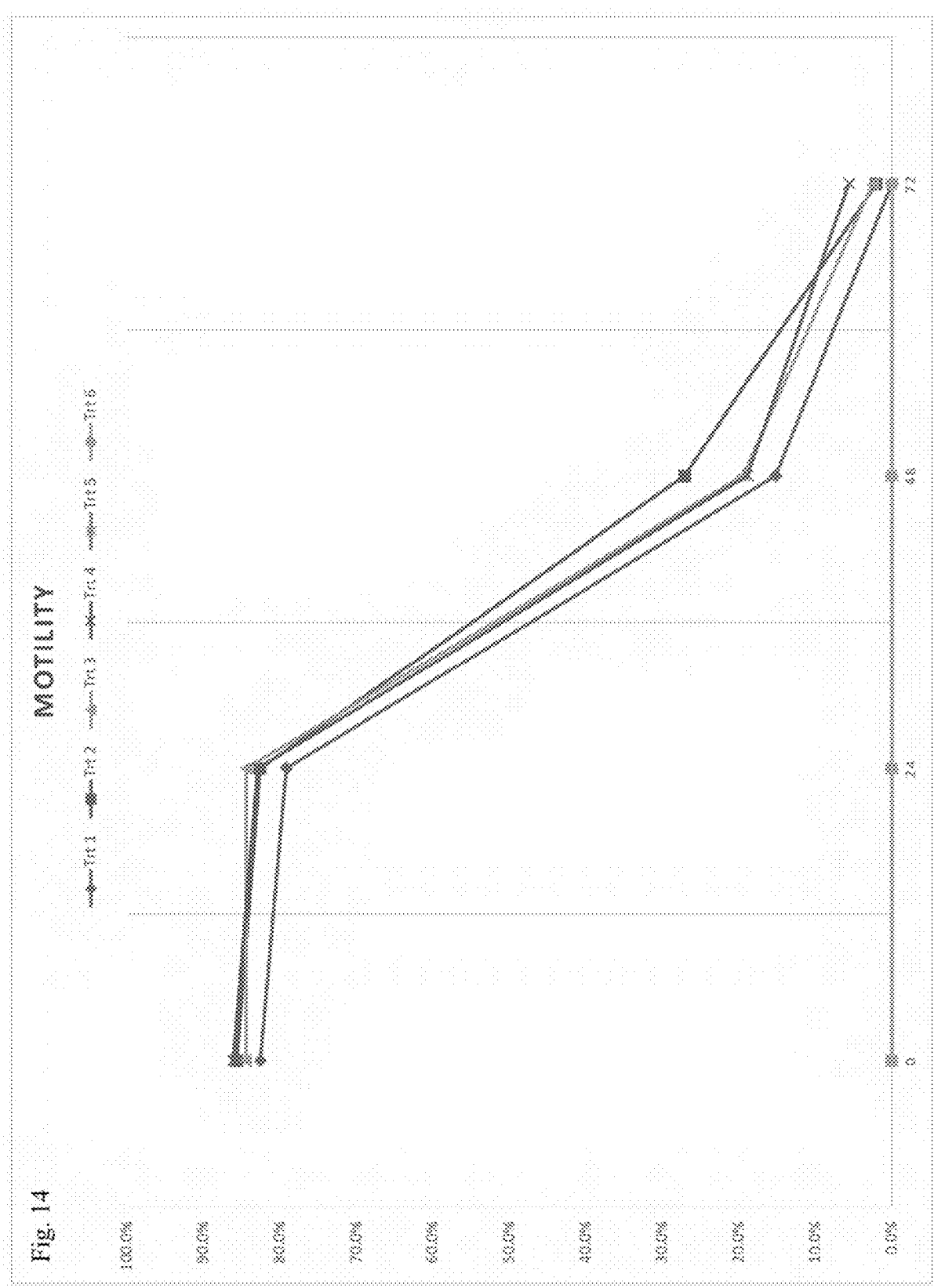
FIG. 14 is a graphical depiction of the post-sort sperm motility of different treatment groups in Example 5 over time.
Figure 15:
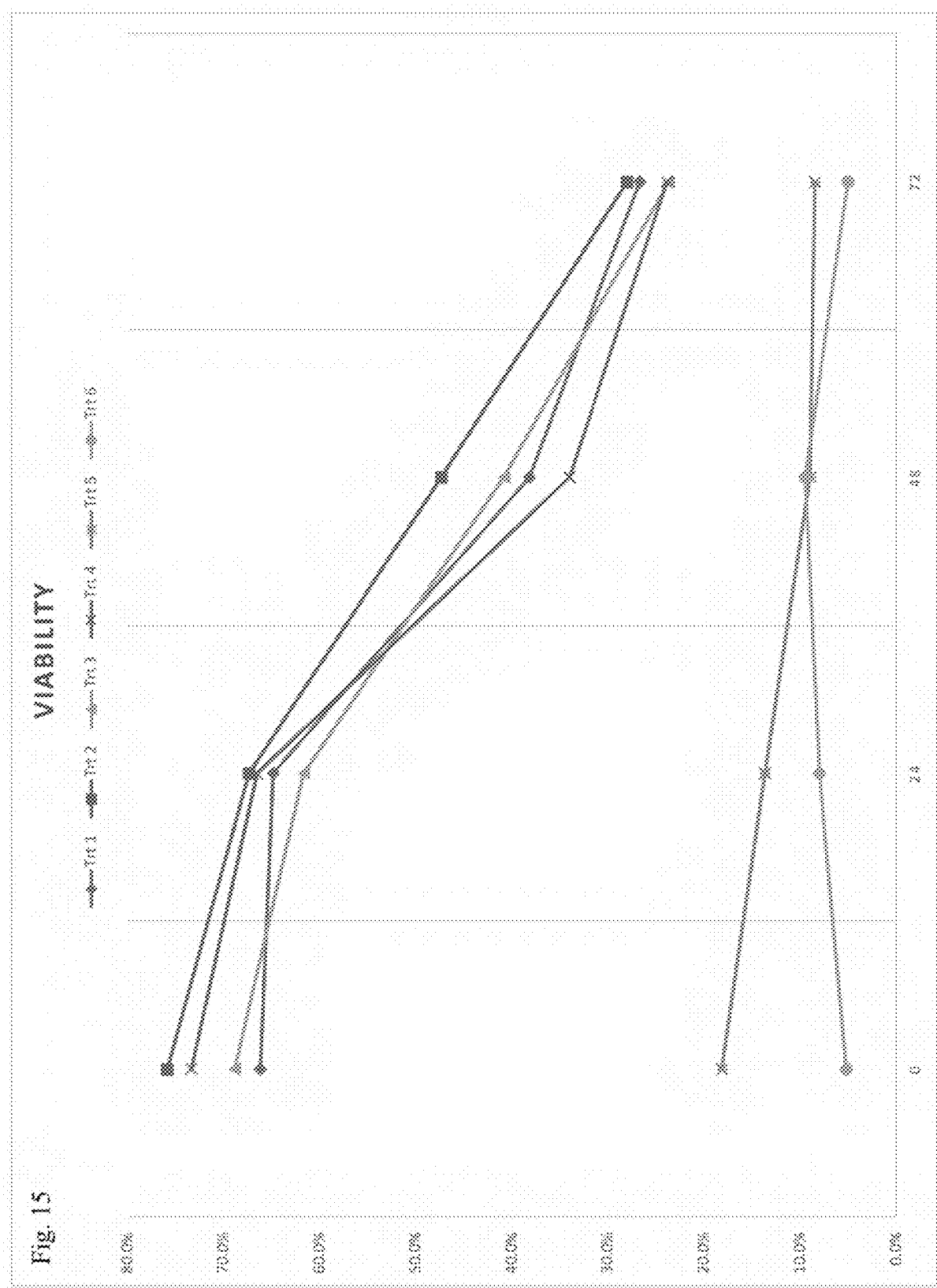
FIG. 15 is a graphical depiction of the post-sort sperm viability of different treatment groups in Example 5 over time.
Figure 16:
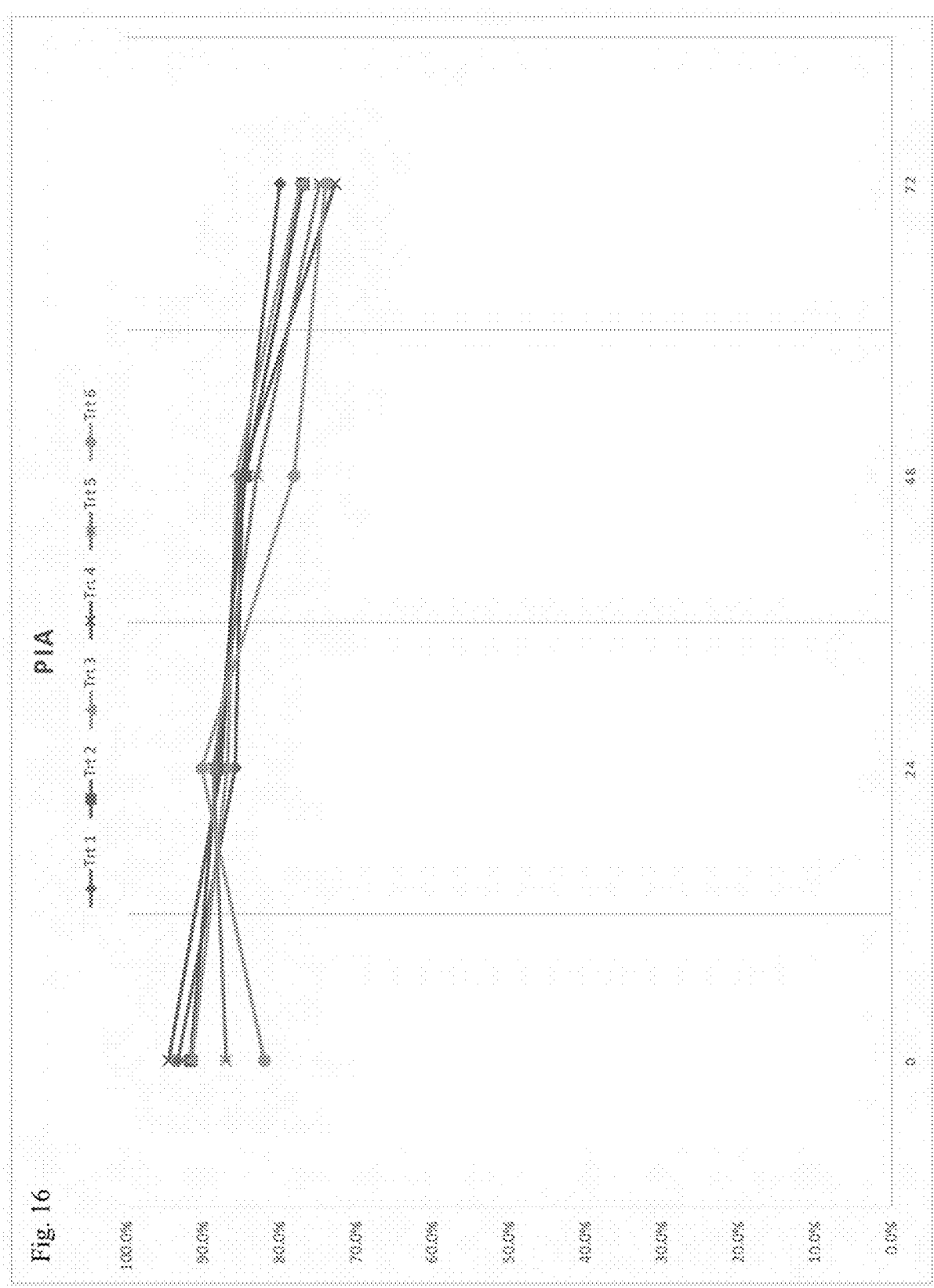
FIG. 16 is a graphical depiction of the percent intact acrosomes of different treatment groups in Example 5 over time.
Figure 17:
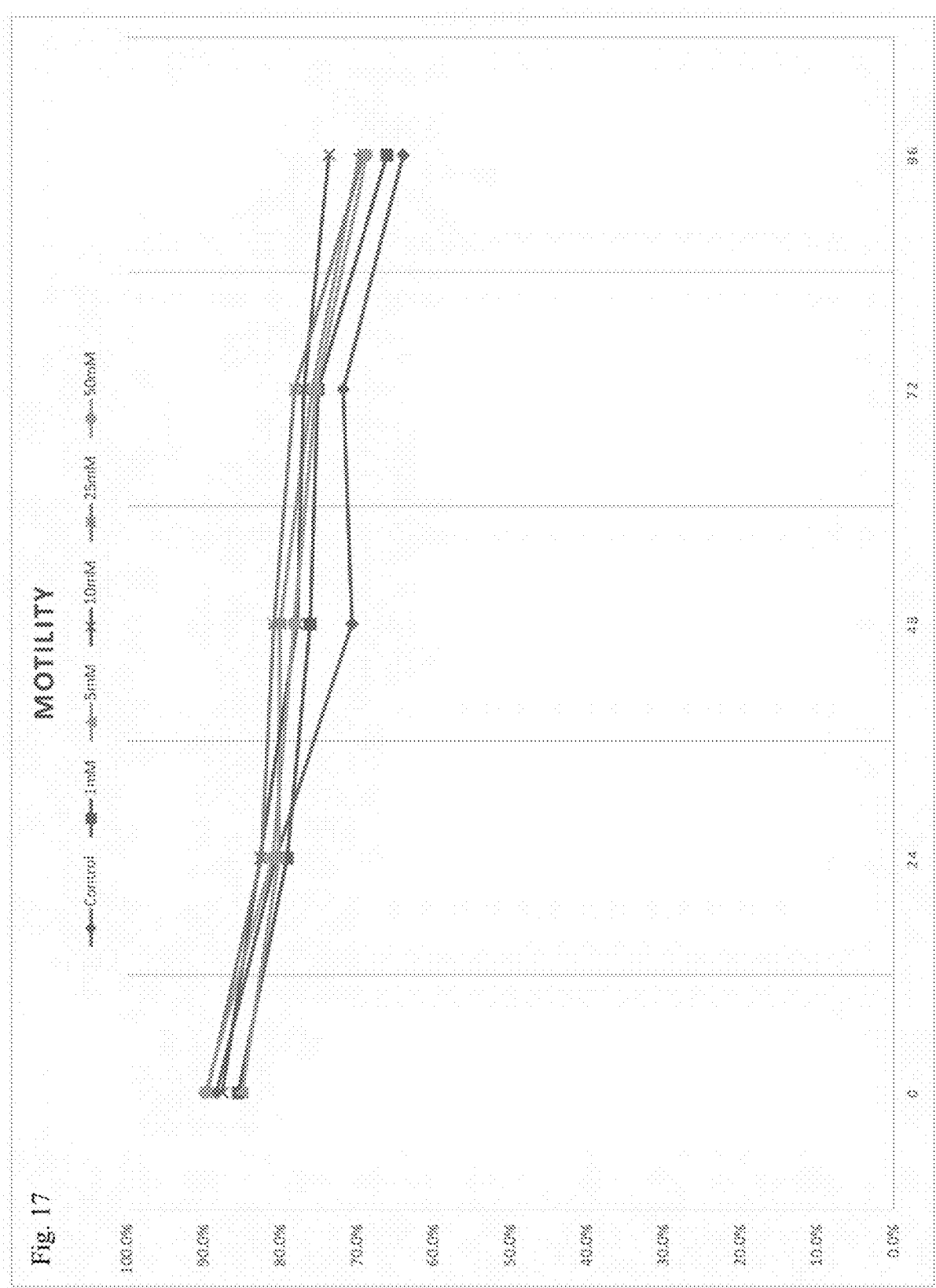
FIG. 17 is a graphical depiction of the post-sort sperm motility of different treatment groups in Example 6 over time.
Figure 18:
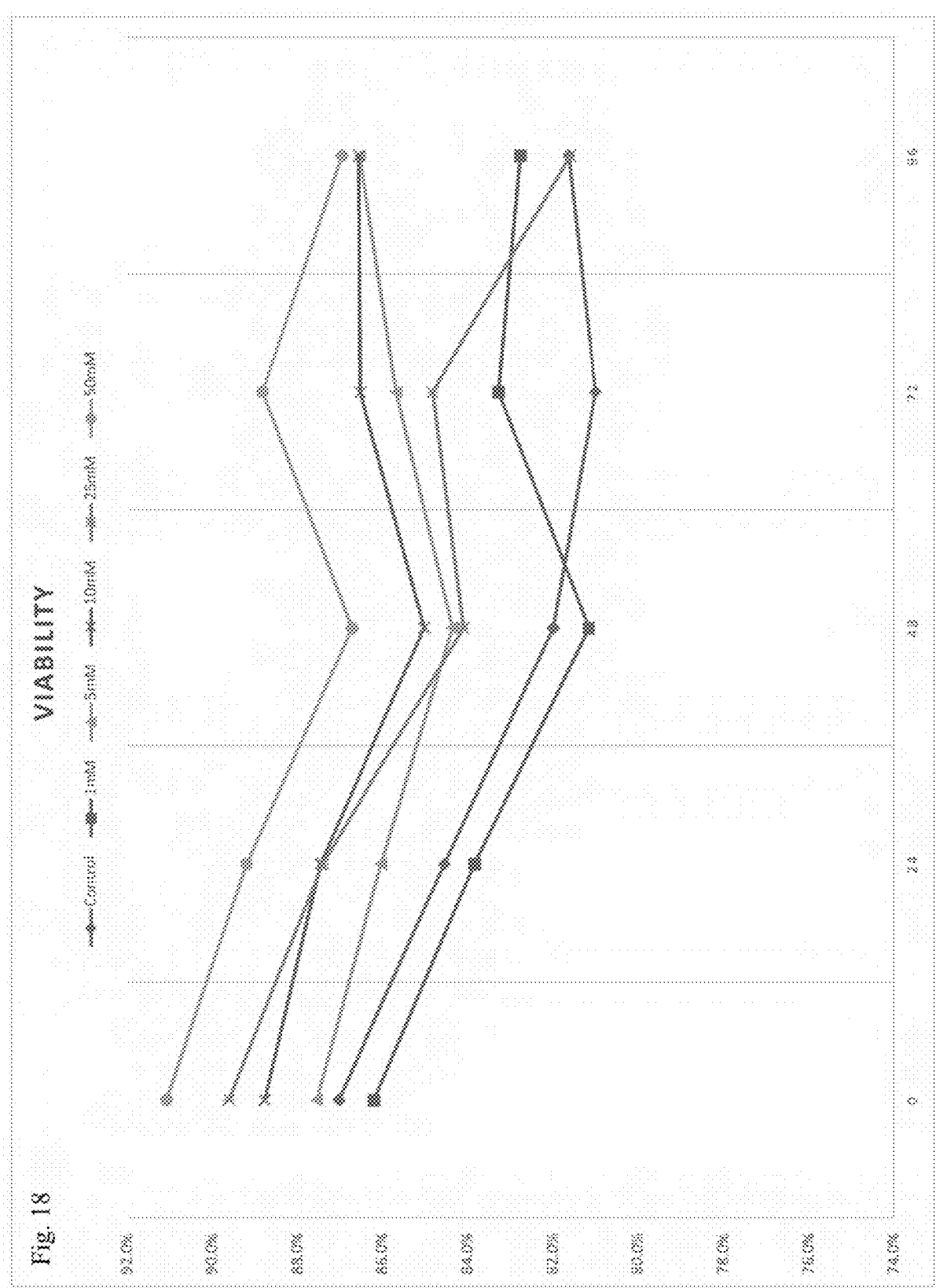
FIG. 18 is a graphical depiction of the post-sort sperm viability of different treatment groups in Example 6 over time.
Figure 19:
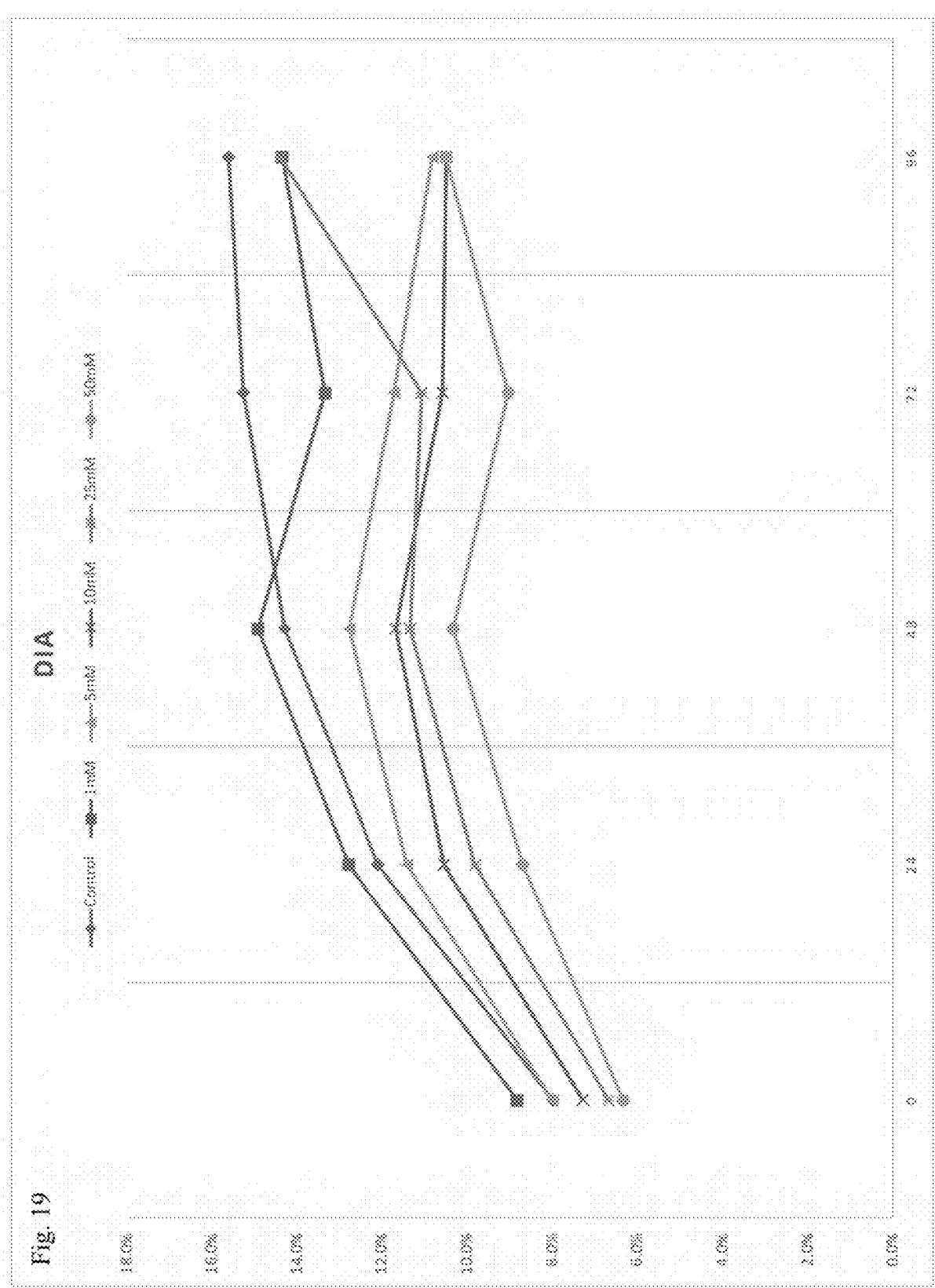
FIG. 19 is a graphical depiction of the dead intact acrosomes of different treatment groups in Example 6 over time.

The invention broadly encompasses methods and compositions comprising low sugar media for processing sperm. It has been discovered that the use of low sugar media for processing sperm improves the overall quality of the sorted sperm, including but not limited to increased motility, viability and fertility. It has further been discovered that the addition of one or more OSRs to low sugar media provides an additional improvement to the quality of processed sperm. Another aspect of the invention relates to the discovery that the use of frozen-thawed, low sugar catch media comprising a cryoprotectant improves the viability of processed sperm.

Processing steps to which sperm are commonly subjected, and with which the invention may be used, include, but are not limited to, collecting from a male animal, which may involve natural, electronic or other types of sexual stimulation; holding; transporting; buffering; chilling; warming; staining; diluting; concentrating; energetically exciting (as with a laser, for example); electronic charging; deflecting; ablating to kill unwanted cells usually with targeted lasers; sorting; collecting; shaking; oscillating; magnetically separating; oxygenating as associated with microchip sorting procedures; labeling; precipitating; centrifuging; resuspending; mixing; dialyzing; cryostabilizing; freezing; vitrifying; cryopreserving; thawing; culturing; inseminating; microinjecting; microfluidic processing; microchip processing; jet and air processing; flow cytometry processing; and similar handling techniques.

Regardless of how sperm are to be ultimately utilized, the initial processing step is typically collection of a sperm sample from a male. Generally, the sperm sample is collected into an extender or diluent designed to sustain the cells until further processing or use. Alternatively, semen is collected and then subsequently diluted with an extender after collection. One embodiment of the invention encompasses an extender or diluent that comprises low sugar media, which can be used as a storage media or with ART.

Whereas a single processing step, such as collection, may exert only minimal stress on sperm, others or a combination may add significant stress, often killing the cells. An example is the sex sorting process used to separate X- from Y-chromosome bearing cells; the sorting process combines a large number of independent stressful steps that compromise the overall integrity of the sorted sperm population. Accordingly, in a particular embodiment of the invention, low sugar media is used in the sorting process, including but not limited to the staining solution, sheath fluid and catch media, and in the cryopreservation of such processed cells.

I. Collecting Sperm

It is contemplated that intact viable bovine, porcine, equine, ovine, cervine, murine or other mammalian sperm, may be collected and contacted with low sugar media. Various methods of collection of viable sperm are known and include, for example, the gloved-hand method, use of an artificial vagina, and electro-ejaculation. As an example, a bovine sperm sample, typically containing about 0.5 to about 10 billion sperm per milliliter, may be collected directly from the source mammal, or from more than one source mammal of the same species, into a vessel containing low sugar media to form a sperm composition. The low sugar media may optionally comprise one or more OSRs, which may be present as constituents of the low sugar media prior to contacting with the sperm, or which may be added to the sperm composition, each OSR in the concentration range of 0.01 mg/ml to 5 mg/ml.

Once the sperm composition is in the laboratory, various quality checks can be conducted, including checking the motility (e.g., via CASA System), viability (e.g., via flow cytometer), morphology (e.g., via microscopy) and concentration (e.g., via NucleoCounter). Sperm compositions that pass these quality checks can then be prepared for further processing, such as sorting. A comparison of viewing chambers and slides can be done in a variety of IVOS instruments, which for example only can be a Hamilton-Thorne IVOS (Hamilton-Thorne, Beverly, Mass.). Instrument settings may be set as follows: image capture; frames per second=60; number of frames=30; cell detection; minimum contrast=50; minimum cell size=5; defaults, cell size=5; cell intensity=50; progressive cells, path velocity=50 um/s; straightness≥70%; slow cells (um/s); average path velocity (VAP, <30 um/s), straight-line velocity (VSL, <15 um/s). The CASA motility variables measured can be a percentage of total motile sperm (motile), percentage of progressively motile sperm (progressive), VAO, VSL, curvilinear velocity (VCL, um/s), average lateral head displacement (ALK, um) and the number of times the sperm head crosses the mean path/s (BCF, Hz), straight-line sperm motility (STR, %), and linear sperm motility (LIN, %). See for instance, Lenz, R W, et al., J AnimSci (2011) 89:383-388, incorporated by reference herein in its entirety.

Various OSRs can be used in the context of the current invention, including but not limited to catalase, superoxide dismutase (SOD), SOD mimics, glutathione, glutathione reductase, glutathione peroxidase, pyruvate, mercaptoethanol, butylated hydroxytoluene (BHT), lipoic acid, flavins, quinines, vitamin K (and related vitamers), vitamin B12 (and related vitamers), with 'vitamers' defined as compounds having the same vitamin activity (such as cobalamin, cyanocobalamin, methylcobalamin, adenosylcobalamin, hydroxocobalamin, and pseudo-B12), vitamin E (including its vitamers, tocopherols ($\alpha$, $\beta$, $\gamma$), tocotrienols, and $\alpha$-tocopheryl), alpha-ketoglutarate (also known as $\alpha$-KG, AKG or oxo-glutarate) and various biological forms of AKG (such as arginine, aspartate, lysine, and similar derivatives), other compounds that regulate nitric oxide in the cell including malondialdehyde (MDA) and asymmetric dimethylarginine (ADMA); and biologically active derivatives thereof.

Alternatively, the semen sample may be collected into an empty vessel and then subsequently contacted with low sugar media within several minutes to hours after collection to form the sperm composition. In addition to a buffer, the sperm composition may also contain a range of additives, including but not limited to the aforementioned OSRs, chelators, tricarboxylic acid cycle intermediates, cryoprotectants, sterols, lipids, fatty acids, protein sources, antibiotics, growth factors, caproic acid, catalase, Caprogen (caproic acid, catalase, and 5% egg yolk) detergents, including alkyl ionic detergents such as sodiumdodecyl sulfate (SDS). It should be noted that certain substances may be classified in one or more of the above listed categories of additives. For example, citrate may be considered both a tricarboxylic acid cycle intermediate and a buffer.

Exemplary buffers for use in the invention include, but are not limited to, carbonates, phosphates, citrates, acetates, lactates, and combinations thereof. Specific buffers that may be used include, but are not limited to, Tris, TES, Pipes, HEPES, TALP, TCA, PBS, citrate, milk and derivatives thereof, which are discussed in detail in U.S. Pat. No. 7,208,265 the contents of which is hereby incorporated by reference in its entirety.

Exemplary chelators for use in the invention include, but are not limited to, deferoxamine, deferasirox, penicillamine, alpha lipoic acid, DMPS, DMSA, dimercaprol and aminopolycarboxylic acids (complexones), including but not limited to Fura-2, IDA, NTA, EDTA, DTPA, EGTA, BAPTA, NOTA, DOTA and nicotianamine, and derivatives thereof.

Exemplary tricarboxylic acid cycle intermediates for use in the invention include, but are not limited to, pyruvate, acetyl-CoA, citrate, isocitrate, $\alpha$-ketoglutarate, succinyl-CoA, succinate, fumarate, malate, oxaloacetate, and derivatives thereof, including but not limited to isomers and acids. In a particular embodiment, low sugar media comprises two or more tricarboxylic acid cycle intermediates, including but not limited to, pyruvate, acetyl-CoA, citrate, isocitrate, $\alpha$-ketoglutarate, succinyl-CoA, succinate, fumarate, malate, oxaloacetate, and derivatives thereof, including but not limited to isomers and acids.

Exemplary cryoprotectants for use in the invention include but are not limited to propylene glycol, dimethyl sulfoxide, ethylene glycol and glycerol, or a combination thereof. In certain embodiments, low sugar media may comprise a concentration of cryoprotectant by percent volume (w/v) selected from the following: 1-5%; 5%; 5 to 10%; 10%; 10 to 20%; 16.7%; 20%; 20 to 30%; or 30 to 40%.

Exemplary protein sources for use in the invention include egg yolk, egg yolk extract, milk (including heat homogenized and skim), milk extract, soy protein, soy protein extract, serum albumin, bovine serum albumin, human serum substitute supplement, seminal proteins, such as, for example, whole seminal plasma or seminal plasma extracts (see, for example, Parks et al., Sperm Membrane Phospholipid Peroxidation and Fragmentation: Effects on Sperm Function and Role of Seminal Plasma PAF-Acetylhydrolase, Proceedings of the 16th Technical Conference on Artificial Insemination & reproduction, 1996, the content of which is hereby incorporated herein by reference), and combinations thereof. In certain embodiments, low sugar media may comprise a concentration of protein source by percent volume selected from the following: 1-5%; 5%; 5 to 10%; 10%; 10 to 20%; 16.7%; 20%; 20 to 30%; or 30 to 40%. Albumin, and more particularly bovine serum albumin (BSA), is a commonly used protein source. For example, if included, BSA may be present in the sperm composition in an amount of, less than about 5.0% (w/v); less than about 2% (w/v); less than about 1% (w/v); or about 0.1% (w/v).

The use of a protein source, such BSA, alone may initiate the process of capacitation in a percentage of the sperm in the composition. It is generally preferred that this process take place in the female reproductive tract. Therefore, in order to inhibit the initiation of capacitation during dilution, as well as during subsequent processing step such as staining and sorting, an alternative protein source or a protein substitute may be included in the sperm composition. The alternative protein source or protein substitute possess the advantageous effects of a typical protein source, such as BSA, in addition to the ability to inhibit the initiation of capacitation in a larger percentage of the cells in the sperm composition. Examples of a alternative protein sources includes human serum substitute supplement (SSS) (Irvine Scientific, Santa Ana, Calif.) and cholesterol enhanced BSA, while an example of a protein substitute includes a polyvinyl alcohol, such as for example, a low to medium viscosity polyvinyl alcohol generally of a molecular weight of about 30,000 to about 60,000. Generally, if included, these compositions will be present in the same amounts as disclosed above with respect to BSA, with the total albumin content of the buffer or buffered solution generally not exceeding about 5.0% (w/v).

An antibiotic may be included in the sperm composition in order to inhibit bacterial growth. Exemplary antibiotics include, for example, tylosin, gentamicin, lincomycin, spectinomycin, Linco-Spectin® (lincomycin hydrochloride-spectinomycin), penicillin, streptomycin, ticarcillin, polymyxin B, or any combination thereof. If included, the antibiotics may be present in a concentration of about 50 µg to about 800 µg per ml of semen, regardless of whether the semen is neat, buffered, or contains additional substances, such as for example, any of the additives mentioned herein. The Certified Semen Services (CSS) and National Association of Animal Breeders (NAAB) have promulgated guidelines regarding the use of antibiotics with respect to sperm collection and use.

A growth factor may be added to the sperm composition in order to help maintain the viability of the sperm. Exemplary growth factors include, for example, transforming growth factors ("TGF"), such as, for example, TGFβ-1 and TGFβ-2, and insulin-like growth factors ("IGF"), such as for example, IGF-1. Generally, TGF may be present in the sperm composition in the form of TGFβ-1 in a concentration of about 0.1 ng/L to about 10 µg/L or as TGFβ-2 in a concentration of about 0.1 ng/L to about 200 ng/L, and IGF may be present in the sperm composition in the form of IGF-1 in a concentration of about 0.1 ng/L to about 50 µg/L. The use of such growth factors is well known in the art and is disclosed, for example, in U.S. Patent Application Publication No. 2003/0157473, the content of which is hereby incorporated herein by reference.

Once collected, the sperm may be stored in low sugar media for a desired period of time or alternatively, may be used and/or further processed within several hours. In either event, the cells may be used, for example, in a staining process, a sorting process, or a fertilization process. It is contemplated that any such further use and/or processing of the sperm may utilize low sugar media.

II. Sorting of Collected Sperm

A. Staining of the Cells

One embodiment of the invention encompasses the use of low sugar media in a staining solution for sperm. A process of staining sperm typically comprises the formation of a staining solution containing intact viable sperm and a dye, sometimes referred to as a label. In this aspect of the invention, the low sugar media may be contacted with the sperm to form a sperm composition, and then the sperm composition contacted with a DNA selective dye to form the staining solution. Alternatively, a DNA selective dye may be added to a low sugar media to form a staining solution, with sperm subsequently added to the staining solution.

In this embodiment, the sperm source may be neat semen, or alternatively, a sperm-containing semen derivative obtained by centrifugation or the use of other means to separate semen into fractions.

The pH of the staining solution may be maintained at any of a range of pHs; typically this will be in the range of about 5.0 to about 9.0, or in the range of 5.5 to 7.8. The staining solution may be maintained at a slightly acid pH, i.e., from about 5.0 to about 7.0. Typically, the pH is from about 6.0 to about 7.0; from about 6.0 to about 6.5; about 6.2, about 6.5; about 6.6; about 6.7; about 6.8; about 6.9; or about 7.0. Alternatively, the staining solution may be maintained at a slightly basic pH, i.e., from about 7.0 to about 9.0. Typically, the pH is about 7.0 to about 8.0; about 7.0 to about 7.5; about 7.0; about 7.1; about 7.2; about 7.3; about 7.35; about 7.4; or about 7.5.

The staining solution may be formed by using one or more UV or visible light excitable, DNA selective dyes as previously described in U.S. Pat. No. 5,135,759 and WO 02/41906, the contents of each of which are hereby incorporated herein by reference. Exemplary UV light excitable, selective dyes include Hoechst 33342 and Hoechst 33258. Exemplary visible light excitable dyes include SYBR-14 and bisbenzimide-BODIPY® conjugate 6-{[3-((2Z)-2-{[1-(difluoroboryl)-3,5-dimethyl-1H-pyrrol-2yl]methylene}-2H-pyrrol-5-yl)propanoyl]amino}-N-[3-(methyl {3-[({4-[6-(4-methylpiperazin-1-yl)-1H,3'H-2,5'bibenzimidazol-2'-yl]phenoxy}acetyl)amino]propyl}amino)propyl]hexanamide ("BBC") described in WO 02/41906. Each of these dyes may be used alone or in combination; alternatively, other cell permeant UV and visible light excitable dyes may be used, alone or in combination with the aforementioned dyes, provided the dye does not detrimentally affect the viability of the sperm to an unacceptable degree when used in concentrations which enable sorting or enrichment as described elsewhere.

The staining solution may also comprise a dye quencher in addition to a DNA selective dye. Staining protocols for sex sorting, or even bulk sorting, sperm typically rely upon the inclusion of F&DC red food dye No. 40 ("red food dye No. 40" or "red 40") and/or yellow food dye No. 4 as quenching dyes. The maximal absorbance wavelengths of these quenching dyes overlaps the maximal emissions wavelengths of fluorescent dyes, including Hoechst 33342 when bound to nuclear or chromosomal DNA. Because red food dye No. 40 and yellow food dye No. 4 differentially permeate membrane-compromised sperm and overlap the emission spectra of the DNA selective fluorescent dye, FRET (florescence resonance energy transfer) between the light leaving the DNA-stain complex and the dead quenching dye reduces the overall detected intensity of the light emitted from membrane compromised sperm. The quenched, or dampened, fluorescence from these cells provide fewer photons to the detectors resulting in a distinctly lower signal. This distinctly lower signal results in a noticeable separated subpopulation which allows the exclusion ("gating out") of the membrane compromised sperm during the sorting procedure. Since membrane compromised sperm comprises largely non-viable sperm, excluding these cells from the analysis results in an enriched sperm subpopulation with respect to viability in the sex sorted subpopulation.

The staining solution may be formed using fluorescent polyamides, and more specifically polyamides with a fluorescent label or reporter conjugated thereto. Such labels will fluoresce when bound to nucleic acids. Examples of polyamides with a fluorescent label or reporter attached thereto include, for example, those disclosed in Best et al., Proc. Natl. Acad. Sci. USA, 15 100(21): 12063-12068 (2003); Gygi, et al., Nucleic Acids Res., 30(13): 2790-2799 (2002); U.S. Pat. Nos. 5,998,140; 6,143,901; and 6,090,947, the content of each of which is hereby incorporated herein by reference.

Fluorescent nucleotide sequences may also be used to label the sperm. Such nucleotide sequences fluoresce when hybridized to a nucleic acid containing a target or complementary sequence, but are otherwise nonfluorescent when in a non-hybridized state. Such oligonucleotides are disclosed, for example, in U.S. Patent Application Publication No. 2003/0113765 (hereby incorporated herein by reference).

Sex specific antibodies may also be used to label the sperm in a staining solution. In this embodiment, for example, a sex specific antibody may be conjugated with a fluorescent moiety (or equivalent reporter molecule). Because the antibody binds to antigens present on only an X chromosome-bearing or, alternatively, a Y chromosome-bearing cell, such cells can be selectively identified based upon their fluorescence (versus the nonfluorescence of an unlabeled cell). Moreover, more than one sex specific antibody, each antibody having a different fluorescent moiety attached thereto, may be used simultaneously. This allows for differentiation of X chromosome-bearing and Y chromosome-bearing cells based upon the differing fluorescence of each.

Luminescent, color-selective nanocrystals may also be used to label sperm in a staining solution. Also referred to as quantum dots, these particles are well known in the art, as demonstrated by U.S. Pat. Nos. 6,322,901 and 6,576,291, each of which is hereby incorporated herein by reference. These nanocrystals have been conjugated to a number of biological materials, including for example, peptides, antibodies, nucleic acids, streptavidin, and polysaccharides, (see, for example, U.S. Pat. Nos. 6,207,392; 6,423,551; 5,990,479, and 6,326,144, each of which is hereby incorporated herein by reference), and have been used to detect biological targets (see, for example, U.S. Pat. Nos. 6,207, 392 and 6,247,323, each of which is hereby incorporated herein by reference).

The concentration of the DNA selective or of any other type of dye in the staining solution is a function of a range of variables which include the permeability of the cells to the selected dye, the temperature of the staining solution, the amount of time allowed for staining to occur, the concentration of sperm, and the degree of enrichment desired in the subsequent sorting or enrichment step. In general, the dye concentration is preferably sufficient to achieve the desired degree of staining in a reasonably short period of time without substantially detrimentally affecting sperm viability. For example, the concentration of Hoechst 33342, Hoechst 33258, SYBR-14, or BBC in the staining solution will generally be between about 0.1 µM and about 1.0M; from about 0.1 µM to about 1000 µM; from about 100 µM to about 500 µM; from about 200 µM to about 500 µM; or from about 300 µM to about 450 µM. Accordingly, under one set of staining conditions, the concentration of Hoechst 33342 is about 350 µM. Under another set of staining conditions, the concentration of Hoechst 33342 is about 400 µM. Under still another set of staining conditions the concentration is about 450 µM.

As another example, the concentration of a fluorescent polyamide, such as for example, those described in U.S. Application Publication No. 2001/0002314, will generally be between about 0.1 µM and about 1 mM; about 1 µM to about 1 mM; about 5 µM to about 100 µM; or about 10 µM.

Optionally, the staining solution may also contain additives to enhance sperm quality. Exemplary additives include one or more OSRs, an antibiotic, a growth factor or a composition which regulates oxidation/reduction reactions intracellularly and/or extracellularly as discussed above with respect to cell sample collection. These additives may be added to the collection fluid in accordance therewith.

Once formed, the staining solution may be maintained at any of a range of temperatures; typically, this will be within a range of about 4° C. to about 50° C. For example, the staining solution may be maintained at a relatively low temperature, i.e., a temperature of about 4° C. to about 30° C.; in this embodiment, the temperature is about 20° C. to about 30° C.; from about 25° C. to about 30° C.; or about 28° C. Alternatively, the staining solution may be maintained within an intermediate temperature range, i.e., a temperature of about 30° C. to about 39° C.; in this embodiment, the temperature is at about 34° C. to about 39° C.; about 35° C.; or about 37° C. In addition, the staining solution may be maintained within a relatively high temperature range, i.e., a temperature of about 40° C. to about 50° C.; in this embodiment, the temperature is from about 41° C. to about 49° C.; from about 41° C. to about 45° C.; from about 41° C. to about 43° C.; or about 41° C. Selection of a preferred temperature generally depends upon a range of variables, including for example, the permeability of the cells to the dye(s) being used, the concentration of the dye(s) in the staining solution, the amount of time the cells will be maintained in the staining solution, and the degree of enrichment desired in the sorting or enrichment step.

Uptake of dye by the sperm in the staining solution is allowed to continue for a period of time sufficient to obtain the desired degree of DNA staining. That period is typically a period sufficient for the dye to bind to the DNA of the sperm such that X and Y chromosome-bearing sperm may be sorted or enriched based upon the differing and measurable fluorescence intensity between the two. Generally, this will be no more than about 24 hours; no more 30 than about 10 hours; no more than about 2 hours; no more than about 90 minutes; no more than about 60 minutes; or from about 5 minutes to about 60 minutes. In a particular embodiment, the period is about 30 minutes or about 55 minutes.

The length of the staining period and the temperature at which staining occurs are related such that the longer the period of staining, the lower the temperature of staining temperature may be. For example, in one embodiment, the staining may occur at a relatively low temperature and for a period of about 3 hours to about 24 hours. Alternatively, the staining may occur at an intermediate temperature and for a period of about one half hour to about 3 hours. In addition, staining may occur at a relatively high temperature and for a period of about 10 minutes to about 90 minutes. In a particular embodiment, staining may occur at a temperature of about 4° C. for a period of about 24 hours. In another embodiment, staining may occur at a temperature of about 18° C. for a period of about 4 hours. In yet another embodiment, staining may occur at a temperature of about 41° C. for a period of about 30 minutes. In another embodiment, staining may occur at a temperature of about 35° C.

for a period of about 55 minutes. Accordingly, in one embodiment, a staining solution is formed comprising low sugar media, sperm and a dye in a concentration from about 100 µM to about 450 µM, and the staining mixture is held for a period of time at a temperature of about 28° C.; about 35° C.; or about 41° C. In another embodiment, the period of time is about 30 minutes; about 55 minutes; or about 3 hours.

B. Sorting or Enriching of the Stained Sperm

Some embodiments include use of one or more OSRs as pre-mixed components of the prepared buffers, extenders, stains, catch fluids, and/or cryo-extenders used in the sex sorting procedure. In some cases, when the sorting of sperm is not going to involve sex sorting, a quenching dye without the need for a DNA staining dye may be required, in which case the OSR will only be present with the quenching dye to form the stained sample. Commonly used and well known sorting methods include flow cytometry systems, as exemplified by and described in U.S. Pat. Nos. 5,135,759, 5,985,216, 6,071,689, 6,149,867, and 6,263,745; International Patent Publications WO 99/33956 and WO 01/37655; and U.S. patent application Ser. No. 10/812,351 (corresponding International Patent Publication WO 2004/088283), the content of each of which is hereby incorporated herein by reference. When sorting according to such methods, the sperm are introduced into the nozzle of a flow cytometer in a sample fluid. In one embodiment, therefore, the sample fluid may comprise low sugar media and the stained sperm.

As noted above, in certain embodiments of the invention, sex sorting of sperm may be accomplished using any process or device known in the art for cell analysis, sorting and/or population enrichment including but not limited to use of a flow cytometer or use of a microfluidic chip, and encompasses techniques for physically separating X and Y bearing sperm from each other, as with droplet sorting and fluid switching sorting, and techniques for gender enrichment in which sperm bearing the undesired sex chromosome are killed, immobilized, or otherwise rendered infertile, such as by use of laser ablation/photo-damage techniques.

Generally, in certain embodiments, devices used with the invention determine a property of sperm based on fluorescence emitted by the sperm when passed before a source of illumination such as a laser beam. The presence or absence of an X- or Y-bearing chromosomes are examples of such a property. Other properties include but are not limited to viability, motility, intact or damaged membranes, genetic defects, the presence or absence of specific genes or gene markers, morphology and fertility. In certain embodiments, the user decides the property or properties the device will analyze and select for, referred to as a property, or properties, of interest. For example, in one embodiment of the invention, if the property of interest is the presence of a Y-bearing chromosome in sperm, the devices used with the invention can analyze sperm and then select the sperm having the property of interest by, for example, photo-damaging/laser ablating the sperm having the property of interest. Alternatively, the devices used with the invention can photo-damage/laser ablate the sperm without the property of interest, leaving the sperm having the property of interest in tact. In other embodiments, the devices of invention can select sperm having the property of interest by isolating the sperm having the property of interest, by for example, separating, or sorting, the sperm having the property of interest from the sperm without the property of interest. Devices that may be used with the invention include but are not limited to those disclosed above as well as in US Patent Application Publication No. US 2008/0153087 at paragraphs 23-87; paragraphs 99-148; and FIGS. 1-5; and in U.S. Pat. No. 8,206,987 at column 28, line 17 to column 93, line 35; column 126, line 54 to column 130, line 3; and FIGS. 135-138; the disclosures of which are incorporated by reference herein.

In addition to being used in the sample fluid, low sugar media can be used as the sheath fluid used to surround the stream of sample fluid as it travels through a flow cytometer or microfluidic chip, for example. Generally, the sheath fluid may be introduced into a nozzle of a flow cytometer using pressurized gas or by a syringe pump. The pressurized gas is often carbon dioxide or nitrogen. In certain embodiments of the invention, a stream containing sperm to be analyzed may be comprised of a sample fluid and a sheath fluid, or a sample fluid alone.

Optionally, the sample fluid or sheath fluid may also contain an additive, such as, one or more OSRs, an antibiotic or a growth factor, as discussed above with respect to cell sample collection. Each of these additives may be added to either fluid in accordance therewith.

One embodiment of a low sugar sheath fluid comprises Tris(hydroxymethylaminomethane), sodium-citrate dihydrate and citric acid anhydrous. To prepare this low sugar sheath fluid, regardless of the intended volume of sheath fluid desired, the entire quantity of Tris and sodium-citrate are mixed with approximately 95% of the desired volume of ddH$_2$O. Three quarters of the citric acid is also concurrently added. A titration with the remaining quantity of citric acid is performed to reach a specific pH of 6.80. After pH adjustment, ddH$_2$O is added until an osmolarity of 300 mOsm is obtained. One or more OSRs may also be added to this sheath fluid, typically in the range of 0.01 to 5.0 mg/ml.

FIG. 1 illustrates, in schematic form, part of a flow cytometer used to sort a sperm composition to form one or more subpopulations, the flow cytometer being generally referenced as 10. In this particular embodiment of the invention, sex sorting is taking place so the subpopulations are X-chromosome bearing sperm and Y-chromosome bearing sperm.

The flow cytometer 10 of FIG. 1 can be programmed by an operator to generate two charged droplet streams, one containing X-chromosome bearing sperm, charged positively, 12, one containing Y-chromosome bearing sperm, charged negatively 13 while an uncharged undeflected stream of dead cells 14 simply goes to waste.

An operator may also choose to program the flow cytometer in such a manner, that both the X- and Y-chromosome bearing sperm are collected using a "high purity sort" (in other words only live X- and Y-chromosome bearing sperm are collected) or to program the flow cytometer to collect both the X- and Y-chromosome bearing sperm using an "enriched sort" (in other words it will collect droplets containing live cells that were not previously sorted and excluding all initial dead cells again by the use of Boolean Gate logic available with the computer that controls the flow cytometer). The Boolean Gate logic can also be used to collect only one of either the X- or Y-chromosome bearing sperm.

Initially, a stream of sperm under pressure, is deposited into the nozzle 15 from the sperm source 11 in a manner such that they are able to be coaxially surrounded by a sheath fluid supplied to the nozzle 15 under pressure from a sheath fluid source 16. An oscillator 17 which may be present can be very precisely controlled via an oscillator control mechanism 18, creating pressure waves within the nozzle 15 which are transmitted to the coaxially surrounded sperm stream as it leaves the nozzle orifice 19. As a result, the exiting coaxially surrounded sperm stream 20 could eventually and regularly form droplets 21.

The charging of the respective droplet streams is made possible by the cell sensing system 22 which includes a laser 23 which illuminates the nozzle exiting stream 20, and the light emission of the fluorescing stream is detected by a sensor 24. The information received by the sensor 24 is fed to a sorter discrimination system 25 which very rapidly makes the decision as to whether to charge a forming droplet and if so which charge to provide the forming drop and then charges the droplet 21 accordingly.

A characteristic of X-chromosome bearing sperm is that they absorb more fluorochrome dye than Y-chromosome bearing sperm because of the presence of more DNA, and as such, the amount of light emitted by the laser excited absorbed dye in the X-chromosome bearing sperm differs from that of the Y-chromosome bearing sperm and this difference communicates to the sorter discrimination system 25 the type of charge to apply to the individual droplets which theoretically contain only a single X- or Y-chromosome bearing sperm. Dead cells (or those about to die) typically absorb the quenching dye which is communicated to the sorter discrimination system 25 not to apply a charge to the droplets containing such cells.

The charged or uncharged droplet streams then pass between a pair of electrostatically charged plates 26, which cause them to be deflected either one way or the other or not at all depending on their charge into respective collection vessels 28 and 29 to form respectively a gender enriched population of X-chromosome bearing and a gender enriched Y-chromosome bearing sperm having a DNA selective dye associated with their DNA. The uncharged non-deflected sub-population stream containing dead cells (or those about to die) go to the waste container 30.

Alternatively, the cells of a sperm composition may be sorted or enriched using laser steering. This is often referred to as optical trapping or holographic optical trapping. Generally, tightly focused laser light, such as, for example, light focused by a microscope lens, will have a steep intensity gradient. Optical traps use the gradient forces of a beam of light to trap particles based upon the dielectric constant of the beam. To minimize its energy, a particle having a dielectric constant greater than the surrounding medium will move to a region of an optical trap where the electric field is highest. Such devices and methods are described, for example, in WO 2004/012133, U.S. Pat. No. 6,416,190 and related applications and patents, the content of each of which is hereby incorporated herein by reference. The cells of the sperm composition may be sorted accordingly into separate populations, wherein the spermatozoa of the populations comprises a certain percent X chromosome bearing or Y chromosome bearing sperm. Laser ablation/photo damage or fluid switching may also be used to create gender enriched populations.

Any of the steps of the cell sorting process may be carried out within a temperature range selected from the group consisting of about 5° C. to about 15° C.; about 15° C. to about 20° C.; about 20° C. to about 25° C.; about 25° C. to about 30° C.; about 30° C. to about 35° C.; about 35° C. to about 40° C. and about 40° C. to about 45° C.

Furthermore, it is contemplated that sorted or gender enriched sperm of the invention may comprise at least about 65% X chromosome bearing or Y chromosome bearing sperm, at least about 70% X chromosome bearing or Y chromosome bearing sperm, at least about 75% X chromosome bearing or Y chromosome bearing sperm, at least about 80% X chromosome bearing or Y chromosome bearing sperm, at least about 85% X chromosome bearing or Y chromosome bearing sperm, at least about 90% X chromosome bearing or Y chromosome bearing sperm, at least about 95% X chromosome bearing or Y chromosome bearing sperm, at least about 98% X chromosome bearing or Y chromosome bearing sperm, or at least about 99% X chromosome bearing or Y chromosome bearing sperm.

C. Collection of the Sorted Cells into Catch Media

Once sorted, the sorted cells are collected in a vessel that contains a catch media. Generally, the purpose of the catch media includes providing a fluid support for the cells. In one aspect of the invention, the catch media may comprise low sugar media. Optionally, the catch media may further comprise any of the additives as discussed above with respect to cell sample collection, including but not limited to one or more OSRs, cryoprotectants, sterols, lipids, fatty acids and protein sources. If included in the catch media, the sterols, lipids, and fatty acids may be, for example, cholesterol.

Exemplary protein sources include milk (including heat homogenized and skim), milk extract, egg yolk, egg yolk extract, soy protein and soy protein extract. Such proteins may be used in a concentration from about 1% (v/v) to about 30% (v/v), preferably from about 10% (v/v) to about 20% (v/v), and more preferably about 10% (v/v).

Optionally, the catch media may also contain additives such as, an antibiotic, a growth factor or one or more OSRs, as discussed above with respect to cell sample collection. Each of these additives may be added to the catch media in accordance therewith.

One embodiment of a low sugar catch media is prepared by adding the appropriate amount of egg yolk to media comprising Tris(hydroxymethylaminomethane), sodium citrate dehydrate and citric acid anhydrous, mixing and then allowing the mixture set overnight at 5° C. The following day the mixture is centrifuged at 5000 g for 1.5 h. After centrifugation, the top layer of the supernatant is discarded, and the remaining supernatant, which comprises the low sugar catch media, is collected. Finally, one or more OSRs may also be added to the low sugar catch media, typically in the range of 0.01 to 5.0 mg/ml. The low sugar catch media should then be stored at 5° C. until use. Alternatively, the low sugar catch media can be frozen prior to storage and/or shipping. It should be understood that sugar or sugar additive may be added during any of the aforementioned steps for preparing low sugar media including prior to use, prior to freezing or subsequent to thawing of the media.

The sorted cells may be collected into a vessel containing or coated with a cryoextender comprising low sugar media, a cryoprotectant and optionally, any of the additives as discussed above with respect to cell sample collection. Accordingly, in one particular embodiment, the sorted cells are collected into a cryoextender comprising low sugar media and a suitable cryoprotectant.

D. Cryopreservation of the Sorted Cells

Once the sperm have been sorted and caught in collection vessels, they may be used for inseminating female mammals. This can occur almost immediately, requiring little additional treatment of the sperm. In such an instance, the sperm may be stored in their current state for a period of time necessary to, for example, transport them to the location where the insemination is to take place. The sperm may, therefore, be stored and transported in, for example, the catch media.

Likewise, the sperm may be concentrated to a density appropriate for the particular mammalian species, for example, a density of about $10 \times 10^6$ sperm/ml to about $120 \times 10^6$ sperm/ml, in a low sugar media and subsequently stored and transported. The selected density depends upon factors such as those discussed below with respect to fertilization, including the species of mammal from which the sperm were obtained. Such a range of densities based upon the species of mammal from which the sperm were obtained are well known to those of skill in the art.

Likewise, the sperm may also be cooled or frozen for use at a later date. In such instances, the sperm may benefit from the addition of a cryoextender to minimize the impact upon viability or post-thaw motility as a result of cooling or freezing.

A protein source may be added to provide support to the sperm. Examples of common protein sources include milk (including heat homogenized and skim), milk extract, egg yolk, egg yolk extract, soy protein and soy protein extract. Such proteins may be found in a concentration from about 3% (v/v) to about 30% (v/v); from about 10% (v/v) to about 20% (v/v); or about 20% (v/v).

A cryoprotectant is preferably included in the cryoextender to lessen or prevent cold shock or to maintain fertility of the sperm. Numerous cryoprotectants are known in the art. Selection of a cryoprotectant suitable for use with a given extender may vary, and depends upon the species from which the sperm to be frozen were obtained. Examples of suitable cryoprotectants include, for example, glycerol, dimethyl sulfoxide, ethylene glycol, propylene glycol, trehalose, Triladyl®, and combinations thereof. If included, generally, these cryoprotectants are present in the cryoextender in an amount, by percent volume, of about 1-5%; 5%; about 5 to 10%; about 10%; about 10 to 20%; about 16.7%; about 20%; about 20 to 30%; or about 30 to 40%.

Optionally, the cryoextender may also contain additives as discussed above with respect to cell sample collection, including but not limited to an antibiotic, a growth factor, or one or more OSRs. Each of these additives may be added to the cryoextender in accordance therewith.

The following method of freezing porcine sperm can be used with the invention, but is presented by way of example only—any suitable cryopreservation method known in the art can be used.

After sorting, 50 ml tubes containing the sex sorted sperm (each with 20 million cells) can be divided into tubes of 15 ml, with approximately 12 ml of a sex-select sperm sample in each tube, each containing approximately 10 million sex sorted sperm. Theses tubes can be centrifuged at 3076 g at 21° C. for 4 minutes. The supernatant decanted, and the pellet can remain with some of the supernatant in approximately 50 µl.

To each pellet, a first cooling medium that may comprise a solution of 20% egg yolk and/or lactose can then be added at room temperature. The motility of the sperm can then be checked. If acceptable, the tubes can be taken to a programmable temperature control machine (PolyScience—Mini-Tube) or can be manually handled to decrease the temperature from about 21° C. to about 5° C. over a period of about 2 hours. After the timed temperature shift with the cells at 5° C. a freezing medium is added to the cells, which may comprise egg-yolk, lactose, glycerol and EquexPasteStem, or may just comprise a cryoprotectant such as glycerol, or the cryoprotectant with an osmotic stabilizer which is previously cooled to 5° C. is added to the samples. After 10 minutes, the sex sorted sperm composition can be placed in artificial insemination straws, and the straws then exposed to liquid nitrogen vapors (approximately 4 cm from the liquid nitrogen) for a short period of time (e.g. 10 minutes) or cryopreserved in programmable freezer and then placed directly into the liquid nitrogen for long term preservation.

When the sex sorted sperm compositions are ready for use, the straws can be unfrozen by thawing/warming the straws (e.g. place in a water bath set at about 37° C. for about 1 minute or 50° for 20 seconds). Post-thaw, motility and viability of the sperm can then be analyzed at 30, 90 and/or 150 minutes for standard comparisons.

III. Storage of the Collected Cells

A. Storage Period

Once the sperm have been collected from the source male, regardless of whether they are optionally sorted thereafter, the sperm may be stored for a period of time in low sugar media. The period of storage is dependent upon several factors, including for example, the temperature at which the cells are stored, the number of cells within the storage container, whether the sperm are sorted or unsorted or have been previously been subjected to other processes such as cryopreservation, the method of fertilization for which the cells will be used, and the female mammal being fertilized.

Generally, for example, the sperm may be stored for several hours, such as for example, 2, 4, 8, 12, or 24 hours; for several days, such as for example 1, 2, 3, 4, 5, 6, or 7 days; several weeks, such as for example, 1, 2, 3, or 4 weeks; or several months, such as for example, 1, 2, or 3 months. Typically, sperm may be stored for several hours to several days at a temperature of about 0° C. to about 30° C.; for several days to several weeks at a temperature of about −4° C. to about 5° C.; and for several weeks to several months at a temperature of about −196° C. (in liquid nitrogen vapor) to about −4° C. For porcine sperm, for example, a sample can be held at a temperature of 0-39° C. (typically 16-17° C.) for between about 12 hours to about 18 hours while it is being shipped from the collection point to the point of further processing or use. In other embodiments of the invention, the sample can be held at a temperature of 0-39° C. (typically 16-17° C.) for more than 18 hours.

B. Storage Temperature

The sperm, whether sorted or unsorted, may be stored at a range of different temperatures. Selection of a storage temperature is dependent upon several factors, such as for example, the length of time for which the sperm will be stored, the concentration of sperm within the storage container, whether the sperm are sorted or unsorted, the method of fertilization for which the sperm will be used, and the female being fertilized. All of these factors affect the number of sperm that will remain viable during the storage period. By way of example, generally the greater the length of time for which the sperm may be stored, the lower the temperature at which the sperm may be stored. In certain species, a decrease in temperature generally permits a greater percentage of the stored sperm to remain viable over a longer period of time. In other species, such as with porcine sperm, this may not be true.

Accordingly, sperm may be stored at a temperature of about −196° C. to about 30° C. For example, sperm may be stored at a relatively low storage temperature, i.e., a temperature range of about −196° C. to about −4° C.; in this embodiment, the temperature is typically from about −12° C. to about −4° C.; from about −10° C. to about −4° C.; or about −4° C. Alternatively, the sperm may be stored at an intermediate storage temperature, i.e., a temperature range of about −4° C. to about 5° C.; in this embodiment, the temperature is typically at about −3° C. to about 5° C.; about 0° C. to about 5° C.; or about 5° C. In addition, the sperm may be stored at a moderately high storage temperature, i.e., a temperature range of about 5° C. to about 30° C.; in this embodiment, the temperature is typically from about 10° C. to about 25° C.; from about 12° C. to about 23° C.; from about 15° C. to about 20° C.; or about 18° C.

C. Storage Container

The sperm composition may be stored in a range of different containers. While the containers may vary in size, generally suitable containers will be capable of containing the sperm composition; that is to say, the containers will be constructed of a material that is not susceptible to leaking or deterioration as a result of contact with fluids generally, and sperm compositions specifically, regardless of whether such contact occurs on the inside or outside of the container. Examples of suitable containers include, for example, flasks, beakers, test tubes, ampules, and other such containers that are generally constructed of glass, plastic, or other similar materials. In a particular embodiment, the container is of a type of construction that is used in the insemination of a female, such as for example, an elongated container. Such elongated containers may generally have a length to diameter ratio of about 1000:1 to about 100:1; a length to diameter ratio of about 900:1 to about 200:1; a length to diameter ratio of about 800:1 to about 300:1; a length to diameter ratio of about 700:1 to about 400:1; a length to diameter ratio of about 600:1 to about 400:1; a length to diameter ratio of about 500:1 to about 400:1; and in one particular embodiment, a length to diameter ratio of about 450:1. Such elongated containers may generally have a volume of about 0.1 cc to about 100 cc, the volume of the container selected to be used being based upon the species of mammal from which the semen was collected. For example, the volume of such elongated containers may be from about 0.1 cc to about 0.7 cc, preferably a volume of about 0.2 cc to about 0.6 cc, more preferably a volume of about 0.23 cc to about 0.5 cc, and most preferably a volume of about 0.3 cc to about 0.4 cc.

In a particular embodiment, the elongated container is what is commonly referred to in the artificial insemination industry as a straw, having a volume of about 0.23 cc and a length to diameter ratio of about 133:1. In another particular embodiment, the elongated container is what is commonly referred to in the artificial insemination industry as a straw, having a volume of about 0.5 cc and a length to diameter ratio of about 67:1. Typically containers of these volumes are used for the storage of bovine sperm.

Alternatively, the volume of the elongated containers may be from about 1 cc to about 100 cc; about 10 cc to about 75 cc; about 15 cc to about 50 cc; about 20 cc, to about 40 cc; or a volume of about 25 cc to about 30 cc. In a particular embodiment, the elongated container is what is commonly referred to in the artificial insemination industry as a straw, having a volume of about 25 cc and a length to diameter ratio of about 445:1. Typically, containers of this volume are used for the storage of porcine sperm.

The advantage of storing the sperm composition in a straw is that the composition may remain stored therein until it is to be used for insemination of a female, at which time the contents of the straw may be placed into the uterus of a female.

IV. Fertilization or Insemination

Another aspect of the present invention is the fertilization of an egg or insemination of a female, generally employing the novel process for storing spermatozoa as described above.

Once a sperm composition has been formed as discussed in greater detail above with respect to the collection of a sperm sample, the sperm composition may be used to inseminate a female. Insemination may be performed according to any of a number of ART methods well known to those of skill in the art. These methods include, for example, artificial insemination, including standard artificial insemination, deep uterine insemination and laparoscopic insemination, and other methods well known to those of skill in the art. For example, a sperm composition comprising low sugar media and one or more OSRs may be used to inseminate a female, such as for example, by artificial insemination. In a particular embodiment, the sperm composition may be in an elongated container for use in the insemination of a female mammal.

Alternatively, the sperm composition may be used to fertilize an egg, and more particularly, an egg in vitro, such as for example, by microinjection, including intracytoplasmic sperm injection (ICSI), and other methods well known to those in the art. The fertilized egg may thereafter be introduced into the uterus of a female by any of a number of means well known to those of skill in the art, such as for example embryo transplant. In another aspect of the invention, zygotes and/or embryos from artificially inseminated females can be recovered and then cultured and/or cryopreserved/vitrified.

Insemination of a female mammal or fertilization of an egg in vitro (followed by introduction of the fertilized egg into the uterus of a female) using a sperm composition may occur shortly after formation of the sperm composition, such as for example, within about 120 hours; within about 96 hours; within about 72 hours; within about 48 hours, and in a particular embodiment, within about 24 hours after formation of the sperm composition. In such instances, generally the sperm compositions may not have been cryopreserved prior to insemination of a female or fertilization of an egg in vitro (i.e., the composition is fresh or comprises fresh sperm) instead it may have been refrigerated at temperatures of about 4° C. to about 25° C.; about 10° C. to about 25° C.; about 15° C. to about 20° C.; or about 18° C. Alternatively, the sperm composition may be cryopreserved and then thawed prior to insemination of a female or fertilization of an egg in vitro (i.e., the dispersion is frozen/thawed or comprises frozen/thawed sperm). Typically, in such an instance, the cryopreserved sperm composition will be thawed immediately, such as, for example, within about 15 minutes, before insemination of a female or fertilization of an egg in vitro. Alternatively, the cryopreserved dispersion may be thawed over a period of time or thawed and subsequently stored for a period of time, such as for example less than about 5 days; less than about 2 days; less than about 1 day; or less than about 12 hours.

V. Freezing Low Sugar Media Comprising a Cryoprotectant

One aspect of the instant invention relates to the discovery that low sugar media comprising a protein source, such as egg yolk, that is frozen and thawed prior to use in processing sperm, increases the viability of the processed sperm. A specific application of this discovery encompasses the use of such frozen-thawed low sugar media during the cell sorting process and, in particular, as a catch fluid.

Additionally, prior to this discovery, media comprising a protein source, such as egg yolk, was typically made at the facility where it was to be used due to the fact that freezing such media prior to use in sperm processing generally resulted in lower quality sperm. Accordingly, the discovery has an additional benefit in that the use of low sugar media allows for the shipping of such media to a destination in a frozen state, where it can then be thawed and used without any deleterious effects compared to media with higher sugar content that has not been frozen. To the extent the same type of sperm processing is being carried out in multiple, geographically distant lab facilities, media with higher sugar content comprising a protein source such as egg yolk becomes a variable in processing since the perishable constituents of the media, such as the egg yolk, must generally be obtained locally. Accordingly, the ability to ship frozen media comprising perishable and otherwise highly variable components, such as egg yolk, from a centralized manufacturing facility allows for better quality control across multiple, geographically separate lab facilities where the media will be used.

Example 1

The following Example demonstrates the effect of freezing and thawing low sugar catch media prior to use in sorting boar sperm.

A. Collection

The sperm-rich fraction of ejaculates from ten boars was collected into a collection bag using the gloved-hand technique. The motility and morphology of each ejaculate was evaluated by CASA whereas sperm morphology was evaluated by a trained technician counting a minimum of 100 cells. Ejaculates with greater than 85% motile cells and greater than 80% normal morphological cells were diluted in a Tris-citrate media (maintained at 36° C.) to form a sperm composition having a sperm concentration of 100 million cells/mL. Each sperm composition was then placed in a semen tube, bottle or bag and cooled to 17° C. prior to transport to the sorting facility in thermal coolers containing frozen gel packs.

B. Sex Sorting

At the sorting facility, the sperm composition was checked for motility and morphology. 5 μl/1 mL of Hoechst 33342 (5 mg/ml in MiliQ water; Ref: B-2261) was added to normal sperm compositions to form a staining solution. The staining solution was then incubated for 55 minutes at 35° C. After incubation the staining solution was placed in a dark place at room temperature (21-22° C.). Immediately prior to sorting, the staining solution was filtered (CellTricks of 0.50 μm) and either 1 μl of yellow food dye No. 6 or red food dye (25 mg/ml inMiliQ water) was added to the solution to form a sample fluid. The sample fluid was then sorted in a Genesis III flow cytometer (CytonomeST, Boston, Mass.) with an event rate at 20-25,000 million/sec. Sorted sperm were collected in 50 ml tubes containing 2.5 ml of catch media for every 20 million cells, centrifuged at 2400 g for 3 minutes and then resuspended in a Tris-citrate media.

C. Experimental Conditions

In this Example, sorted sperm were collected into three types of catch media: a low sugar "Control" media, containing Tris, sodium citrate, citric acid and 16.7% egg yolk; a low sugar "Freeze" media, containing Tris, sodium citrate, citric acid and 16.7% egg yolk, and which was frozen and then thawed prior to use; and a "+Sugar" media, containing fructose, Tris, citric acid and 16.7% egg yolk.

After resuspension, motility (assessed by CASA) and viability (assessed by LIVE/DEAD Viability/Cytotoxicity Kit; Molecular Probes, Inc.) of the sorted sperm were determined at 0, 24, 48, 72, 96 and 144 hours. Results for each treatment group ("Trt") are shown in Tables 1 through 4 below. There was not a treatment by time effect so values at each time were pooled in Tables 2 and 4.

TABLE 1

| Motility (PSE = 3.41) | | | | | | |
|---|---|---|---|---|---|---|
| Trt | 0 h | 24 h | 48 h | 72 h | 96 h | 144 h |
| Control | 91.84 | 91.75 | 88.02 | 85.33 | 80.11 | 64.82 |
| +Sugar | 91.19 | 90.48 | 86.41 | 84.23 | 79.62 | 55.15 |
| Freeze | 92.83 | 92 | 89.5 | 87.42 | 81.42 | 63.55 |

TABLE 2

| Trt | Motility | SE |
|---|---|---|
| Control | 82.69 | 1.03 |
| +Sugar | 80.47 | 1.03 |
| Freeze | 82.84 | 1.03 |

| Variable | P Value |
|---|---|
| Boar | <0.0001 |
| Trt | 0.214 |
| Time | <0.0001 |
| Trt*Time | 0.814 |

TABLE 3

| Viability (PSE = 1.93) | | | | | | |
|---|---|---|---|---|---|---|
| Trt | 0 h | 24 h | 48 h | 72 h | 96 h | 144 h |
| Control | 87.07 | 87.74 | 79.87 | 78.54 | 76.32 | 66.43 |
| +Sugar | 86.76 | 84.43 | 79.87 | 78.54 | 76.32 | 66.43 |
| Freeze | 90.85 | 89.41 | 85.85 | 84.07 | 79.74 | 71.07 |

TABLE 4

| Trt | Viability | SE |
|---|---|---|
| Control | 80.26 | 0.60 |
| +Sugar | 78.33 | 0.62 |
| Freeze | 82.31 | 0.61 |

| Variable | P Value |
|---|---|
| Boar | <0.0001 |
| Trt | <0.0001 |
| Time | <0.0001 |
| Trt*Time | 0.47 |

Example 2

The following Example compares the post-sort motility, viability and quantitative sorting parameters (peak to valley ration [PVR], sort rate and event rate) in boar semen using sheath fluid and catch media containing Tris, sodium citrate and citric acid (the "Low Sugar" treatment), and sheath fluid and catch media containing fructose, Tris and citric acid (the "Control").

The sperm-rich fraction of ejaculates from eight boars (two replicates) and five boars (tested one time) were collected and then sex sorted using the methods described in Example 1(A) and 1(B) above. Sperm were sorted using either Low Sugar media or the Control media. After resuspension, motility (assessed by CASA) and viability (assessed by LIVE/DEAD Viability/Cytotoxicity Kit; Molecular Probes, Inc.) of the sorted sperm were determined at 0, 24, 48, 72, 96 and 144 hours. Results for motility and viability are shown in Tables 5 through 7 below. There was not a treatment by time effect for viability so data was pooled and expressed in Table 7. The Low Sugar treatment had 32% higher PVR, 23% faster event rate and a 15% faster sort rate.

TABLE 5

Motility (PSE = 1.44)

| Trt | 0 h | 24 h | 48 h | 72 h | 96 h | 144 h |
|---|---|---|---|---|---|---|
| Control | 90.04 | 89.05 | 87.01 | 81.35 | 79.2 | 62.78 |
| Low Sugar | 92.08 | 92.07 | 90.10 | 83.74 | 80.58 | 72.87 |

| Variable | P Value |
|---|---|
| Boar | <0.0001 |
| Trt | <0.0001 |
| Time | <0.0001 |
| Trt * Time | 0.03 |
| Rep | <0.0001 |

TABLE 6

Viability (PSE = 1.36)

| Trt | 0 h | 24 h | 48 h | 72 h | 96 h | 144 h |
|---|---|---|---|---|---|---|
| Control | 87.11 | 79.35 | 78.16 | 70.21 | 69.59 | 63.21 |
| Low sugar | 89.11 | 83.11 | 80.59 | 75.63 | 73.87 | 72.53 |

| Variable | P Value |
|---|---|
| Boar | 0.0019 |
| Trt | <0.0001 |
| Time | <0.0001 |
| Trt * Time | 0.08 |
| Rep | <0.0001 |

TABLE 7

| Trt | Viability | SE |
|---|---|---|
| Control | 74.60 | 0.59 |
| Low sugar | 79.14 | 0.59 |

Example 3

The following Example compares the post-sort motility and viability in boar semen when using media without a sugar additive, media without a sugar additive supplemented with SexedUltra™ (ST Reproductive Technologies, LLC, 2014), or media containing a sugar additive, in the various processing steps for sex sorting sperm. (SexedUltra™ is purported to contain less than 1 g/ml of at least two of the following OSRs: vitamin B12, vitamin B12 vitamers, vitamin E, vitamin E vitamers, tocopherols, tocotrienols, α-tocoperyl, alpha ketoglutarate, and derivatives thereof).

The sperm-rich fraction of ejaculates from six boars (two replicates) were collected using the methods described in Example 1(A) above, except that the diluent employed varied depending on the treatment group, as shown in Table 8. The sperm were sorted using the methods described in Example 1(B), except that the resuspension media varied depending on the treatment group, as shown in Table 8. The sheath fluid, catch media and resuspension media utilized in each treatment group are shown in Table 8 ("EY"=egg yolk). The media indicated in Table 8 comprised the components as follows.

"BTS" media was purchased from a commercial company and the relative ingredients are not known. However, it is a published formula from Pursel and Johnson (1975) that includes 37.0 g/L of glucose; 6.0 g/L of sodium citrate; 1.25 g/L of sodium bicarbonate; 1.25 g/L of EDTA; and 0.75 g/L of KCl. Pursel V G and Johnson L A. 1975. Freezing of boar spermatozoa:fertilizing capacity with concentrated semen and a new thawing extender. J. Anim. Sci. 40:99-102.

"PBS" media contained 8 g/L of NaCl; 0.201 g/L of KCl; 0.204 g/L of $KH_2PO_4$; 1.149 g/L of $Na_2HPO_4$; 0.058 g/L of penicillin; and 0.05 g/L of streptomycin sulphate.

"TTG" media contained 50 g/L of TES; 6.8 g/L of Tris; and 6 g/L of glucose.

"Tris-citrate" media contained Tris, sodium citrate and citric acid.

"Tris-citrate+Glucose" media contained Tris, sodium citrate, citric acid and glucose.

"Tris-citrate+SexedUltra™" media contained Tris, sodium citrate, citric acid and SexedUltra™.

TABLE 8

| Treatment | Diluent | Sheath | Catch | Resuspension |
|---|---|---|---|---|
| 1 | BTS | PBS | TTG with 16.7% EY | BTS |
| 2 | BTS | Tris-citrate | Tris-citrate with 16.7% EY | BTS |
| 3 | BTS | Tris-citrate | Tris-citrate + Glucose with 16.7% EY | BTS |
| 4 | Tris-citrate + SexedUltra ™ | Tris-citrate | Tris-citrate + SexedUltra ™ with 16.7% EY | Tris + SexedUltra ™ |
| 5 | BTS | Tris-citrate | Tris-citrate + SexedUltra ™ with 16.7% EY | BTS |

After resuspension, motility (assessed by CASA) and viability (assessed by LIVE/DEAD Viability/Cytotoxicity Kit; Molecular Probes, Inc.) of the sorted sperm in the five treatment groups were determined at 0, 24, 48, 72, 96 and 120 hours. Results for motility and viability are shown in Tables 9 and 10 below.

TABLE 9

Motility

| Treatment | 0 h* | 24 h | 48 h | 72 h | 96 h | 120 h |
|---|---|---|---|---|---|---|
| 1 | 86.48 | 82.12 | 57.23 | 20.17 | 9.20 | 5.29 |
| 2 | 85.08 | 84.33 | 77.36 | 63.39 | 49.22 | 35.88 |
| 3 | 84.93 | 83.27 | 69.37 | 61.88 | 56.73 | 46.88 |
| 4 | 90.70 | 89.68 | 85.87 | 80.47 | 76.88 | 71.37 |
| 5 | 87.22 | 86.65 | 82.53 | 74.50 | 64.88 | 50.42 |

*0 h = Evaluation of cells immediately after sorting, centrifugation and resuspension.
Pooled standard error = 4.32
P value = trt, time, boar, trt * time <0.0001

TABLE 10

Viability

| Treatment | 0 h* | 24 h | 48 h | 72 h | 96 h | 120 h |
|---|---|---|---|---|---|---|
| 1 | | 76.75 | 61.00 | 15.67 | 11.25 | 10.83 |
| 2 | | 77.92 | 72.83 | 63.33 | 61.42 | 50.08 |
| 3 | | 77.92 | 69.08 | 60.50 | 57.50 | 55.50 |

TABLE 10-continued

| | | Viability | | | | |
|---|---|---|---|---|---|---|
| Treatment | 0 h* | 24 h | 48 h | 72 h | 96 h | 120 h |
| 4 | | 85.92 | 84.50 | 81.83 | 78.33 | 70.83 |
| 5 | | 80.00 | 78.33 | 74.75 | 56.33 | 56.33 |

*0 h = Evaluation of cells immediately after sorting, centrifugation and resuspension.
Pooled standard error = 4.77
P value = trt, time, boar, trt*time < 0.0001

Example 4

The following Example compares the post-sort motility and viability in boar semen when using media without a sugar additive, media without a sugar additive supplemented with SexedUltra™ (ST Reproductive Technologies, LLC, 2014), or media containing a sugar additive, in the various processing steps for sex sorting sperm.

The sperm-rich fraction of ejaculates from two boars were collected using the methods described in Example 1(A) above, except that the diluent employed varied depending on the treatment group, as shown in Table 11. The sperm were sorted using the methods described in Example 1(B), except that the resuspension media varied depending on the treatment group, as shown in Table 11. The sheath fluid, catch media and resuspension media utilized in each treatment group are shown in Table 11 ("EY"=egg yolk). The media indicated in Table 11 comprised the components as follows:

"BTS"; "PBS"; "TTG"; "Tris-citrate"; "Tris-citrate+Glucose"; and "Tris-citrate+SexedUltra™" media contained the components described for each of those media in Example 3, above.

"TCA1" media contained 29.2 g/L of Tris; 11.6 g/L of fumaric acid; and 2000 μL of HCL.

"TCA2" media contained 31.2 g/L of Tris; 11.6 g/L of maleic acid; and 4000 μL of HCL.

TABLE 11

| Trt | Dilution | Sheath | Catch | Resuspension |
|---|---|---|---|---|
| 1 | BTS | PBS | TTG with 20% EY | BTS |
| 2 | BTS | Monsanto | Monsanto with 20% EY | BTS |
| 3 | BTS | Tris-citrate | Tris-citrate with 20% EY | BTS |
| 4 | BTS | Tris-citrate | Tris-citrate + Glucose with 20% EY | BTS |
| 5 | BTS | TCA1 | TCA1 with 20% EY | BTS |
| 6 | BTS | TCA2 | TCA2 with 20% EY | BTS |
| 7 | Tris | Tris-citrate | Tris-citrate + SexedUltra ™ with 20% EY | Tris-citrate |

After resuspension, motility (assessed by CASA), viability (assessed by LIVE/DEAD Viability/Cytotoxicity Kit; Molecular Probes, Inc.) and percent intact acrosomes (PIA) of the sorted sperm in the seven treatment groups were determined at 0, 24, 48, 72, 96 and 120 hours. Results for motility, viability and PIA are shown in Tables 12, 13 and 14, respectively.

TABLE 12

| Trt | Motility (0 h) | Motility (24 h) | Motility (48 h) | Motility (72 h) | Motility (96) | Motility (120 h) | PSE |
|---|---|---|---|---|---|---|---|
| 1 | 91.65 | 72.3 | 15.65 | 0 | 0 | 0 | 9.38 |
| 2 | 29.6 | 0 | 0 | 0 | 0 | 0 | |
| 3 | 71.15 | 12.15 | 0 | 0 | 0 | 0 | |
| 4 | 77.15 | 48.55 | 4.95 | 1.6 | 0 | 0 | |
| 5 | 67.45 | 50.25 | 31.4 | 11.9 | 1.05 | 0 | |
| 6 | 71 | 53.6 | 13.65 | 10.15 | 6 | 2.4 | |
| 7 | 84.05 | 79.45 | 75.35 | 65.05 | 48.9 | 38.05 | |

| Variable | P Value |
|---|---|
| trt | <0.0001 |
| Time | <0.0001 |
| Trt * time | 0.02 |

TABLE 13

| Trt | Viability (0 h) | Viability (24 h) | Viability (48 h) | Viability (72 h) | Viability (96) | Viability (120 h) | PSE |
|---|---|---|---|---|---|---|---|
| 1 | 84.5 | 59.5 | 62 | 46 | 0 | 0 | 8.82 |
| 2 | 66.5 | 61.5 | 0 | 0 | 0 | 0 | |
| 3 | 71.5 | 60.5 | 51 | 0 | 0 | 0 | |
| 4 | 67 | 45 | 46 | 44.5 | 22 | 0 | |
| 5 | 49.5 | 55.5 | 50.5 | 41.5 | 25 | 23.5 | |
| 6 | 62 | 67.5 | 54.5 | 47.5 | 22.5 | 22.5 | |
| 7 | 90.5 | 83.5 | 76.5 | 69 | 72.5 | 76.5 | |

| Variable | P Value |
|---|---|
| trt | <0.0001 |
| Time | <0.0001 |
| Trt * time | 0.0009 |
| Bull | 0.04 |

TABLE 14

| Trt | PIA (0 h) | PIA (24 h) | PIA (48 h) | PIA (72 h) | PIA (96) | PIA (120 h) | PSE |
|---|---|---|---|---|---|---|---|
| 1 | 97.5 | 96 | 92.5 | 89.5 | . | . | 4.44 |
| 2 | 93.5 | 96 | 96 | . | . | . | |
| 3 | 96 | 96.5 | 91.5 | . | . | . | |
| 4 | 94.5 | 85 | 88 | 86 | 86.43 | . | |
| 5 | 83.5 | 84 | 69.5 | 87 | 90.43 | 80.43 | |
| 6 | 90.5 | 92 | 89.5 | 92 | 91.57 | 79.57 | |
| 7 | 92.5 | 95.5 | 90.5 | 88.5 | 84.5 | 91.5 | |

| Variable | P Value |
|---|---|
| trt | 0.02 |
| Time | 0.27 |
| Trt * time | 0.6 |
| Bull | 0.08 |

Example 5

The following Example compares the post-sort motility, viability and PIA in boar semen when using catch media without a sugar additive, media without a sugar additive supplemented with SexedUltra™ (ST Reproductive Technologies, LLC, 2014), or media containing a sugar additive, with or without egg yolk.

The sperm-rich fraction of ejaculates from six boars were collected using the methods described in Example 1(A) above, except that the diluent employed constituted the BTS media described in Example 3. The sperm were sorted using the methods described in Example 1(B), except that the resuspension media also constituted BTS. The catch media utilized in each treatment group are shown in Table 15 ("EY"=egg yolk). The media indicated in Table 15 comprised the components as follows:

"BTS"; "PBS"; "TTG"; "Tris-citrate"; "Tris-citrate+Glucose"; and "Tris-citrate+SexedUltra™" media contained the components described for each of those media in Example 3, above.

"Tris-citrate+Glucose+SexedUltra™" contained Tris, sodium citrate, citric acid, glucose and SexedUltra™.

TABLE 15

| Trt | Dilution | Sheath | Catch | Resuspension |
|---|---|---|---|---|
| 1 | BTS | Tris-citrate | Tris-citrate + Glucose + SexedUltra ™ | BTS |
| 2 | BTS | Tris-citrate | Tris-citrate + SexedUltra ™ with ___% EY | BTS |
| 3 | BTS | Tris-citrate | Tris-citrate + Glucose with EY | BTS |
| 4 | BTS | Tris-citrate | Tris-citrate with EY | BTS |
| 5 | BTS | Tris-citrate | Tris-citrate + Glucose + SexedUltra ™ | BTS |
| 6 | BTS | Tris-citrate | Tris-citrate + SexedUltra ™ | BTS |

After resuspension, motility (assessed by CASA), viability (assessed by LIVE/DEAD Viability/Cytotoxicity Kit; Molecular Probes, Inc.) and DIA (assessed by flow cytometry) of the sorted sperm in the 6 treatment groups were determined at 0, 24, 48 and 72 hours. Results for motility, viability and PIA are shown in Tables 16, 17 and 18, respectively.

TABLE 16

| trt | Motility (0 h) | Motility (24 h) | Motility (48 h) | Motility (72 h) | PSE |
|---|---|---|---|---|---|
| 1 | 82.55 | 79.17 | 15.2 | 0 | 2.74 |
| 2 | 85.62 | 82.58 | 27.08 | 2.03 | |
| 3 | 84.45 | 84.37 | 19.48 | 2.48 | |
| 4 | 86.05 | 82.88 | 18.9 | 5.6 | |
| 5 | 0 | 0 | 0 | 0 | |
| 6 | 0 | 0 | 0 | 0 | |

| Variable | P Value |
|---|---|
| Boar | 0.11 |
| Trt | <0.0001 |
| Time | <0.0001 |
| Trt*Time | <0.0001 |

TABLE 17

| trt | Viability (0 h) | Viability (24 h) | Viability (48 h) | Viability (72 h) | PSE |
|---|---|---|---|---|---|
| 1 | 66.17 | 64.83 | 38.17 | 26.67 | 3.95 |
| 2 | 75.83 | 67.33 | 47.33 | 28 | |
| 3 | 68.83 | 61.67 | 40.83 | 23.67 | |
| 4 | 73.33 | 66.5 | 34 | 23.83 | |
| 5 | 18.17 | 13.67 | 9 | 8.5 | |
| 6 | 5.17 | 8 | 9.5 | 5 | |

| Variable | P Value |
|---|---|
| Boar | 0.002 |
| Trt | <0.0001 |
| Time | <0.0001 |
| Trt*Time | <0.0001 |

TABLE 18

| trt | PIA (0) | PIA (24) | PIA (48) | PIA (72) | PSE |
|---|---|---|---|---|---|
| 1 | 93.33 | 85.83 | 84.83 | 80 | 2.59 |
| 2 | 91.67 | 88.17 | 84.5 | 77 | |
| 3 | 91.5 | 86.83 | 85.67 | 77.33 | |
| 4 | 94.5 | 87.67 | 85.17 | 72.83 | |
| 5 | 87 | 88.67 | 83 | 74.83 | |
| 6 | 82 | 90.17 | 78.17 | 74 | |

| Variable | P Value |
|---|---|
| Boar | 0.1 |
| Trt | 0.08 |
| Time | <0.0001 |
| Trt*Time | 0.236 |

Example 6

Example 6 compares the post-sort motility, viability and dead intact acrosomes (DIA) in boar semen when using sheath fluid and catch media containing increasing amounts of a sugar additive (OmM up to +50 mM glucose).

The sperm-rich fraction of ejaculates from four boars were collected using the methods described in Example 1(A). Two replicates were run for this Example. The sperm were sorted using the methods described in Example 1(B). The sheath and catch media utilized in each treatment group are shown in Table 19 ("EY"=egg yolk). The media indicated in Table 19 comprised the components as follows:

"Tris-citrate" and "Tris-citrate+SexedUltra™" media contained the components described for each of those media in Example 3, above.

TABLE 19

| Trt | Sheath | Catch |
|---|---|---|
| Control | Tris-citrate | Tris-citrate + SexedUltra ™ + 20% EY |
| 1 mM | Tris-citrate + 1 mM Glucose | Tris-citrate + SexedUltra ™ + 1 mM Glucose + 20% EY |
| 5 mM | Tris-citrate + 5 mM Glucose | Tris-citrate + SexedUltra ™ + 5 mM Glucose + 20% EY |
| 10 mM | Tris-citrate + 10 mM Glucose | Tris-citrate + SexedUltra ™ + 10 mM Glucose + 20% EY |
| 25 mM | Tris-citrate + 25 mM Glucose | Tris-citrate + SexedUltra ™ + 25 mM Glucose + 20% EY |
| 50 mM | Tris-citrate + 50 mM Glucose | Tris-citrate + SexedUltra ™ + 50 mM Glucose + 20% EY |

After resuspension, motility (assessed by CASA), viability (assessed by LIVE/DEAD Viability/Cytotoxicity Kit; Molecular Probes, Inc.) and DIA (assessed by flow cytometry) of the sorted sperm in the five treatment groups were determined at 0, 24, 48, 72 and 96 hours. Pooled results for motility, viability and DIA for the two replicates are shown in Tables 20, 21 and 22 below.

TABLE 20

| Trt | Motility 0 h | Motility 24 h | Motility 48 h | Motility 72 h | Motility 96 h |
| --- | --- | --- | --- | --- | --- |
| Control | 88.32 | 80.59 | 70.7 | 71.82 | 63.96 |
| 1 mM | 85.49 | 79.13 | 76.12 | 75.1 | 66.06 |
| 5 mM | 85 | 80.22 | 80.05 | 75.87 | 69.75 |
| 10 mM | 87.58 | 82.65 | 77.82 | 76.95 | 73.67 |
| 25 mM | 89.54 | 82.47 | 80.85 | 78.15 | 69.2 |
| 50 mM | 89.78 | 81 | 78.19 | 75.35 | 68.76 |

PSE = 1.84

| Variable | P Value |
| --- | --- |
| trt | <0.0001 |
| time | <0.0001 |
| Boar | <0.0001 |
| trt*time | 0.25 |

TABLE 21

| Trt | Viability 0 h | Viability 24 h | Viability 48 h | Viability 72 h | Viability 96 h |
| --- | --- | --- | --- | --- | --- |
| Control | 87.03 | 84.55 | 82 | 81 | 81.63 |
| 1 mM | 86.2 | 83.84 | 81.16 | 83.28 | 82.77 |
| 5 mM | 87.55 | 86.03 | 84.36 | 85.68 | 86.54 |
| 10 mM | 88.77 | 87.46 | 85.02 | 86.53 | 86.57 |
| 25 mM | 89.61 | 87.41 | 84.1 | 84.82 | 81.6 |
| 50 mM | 91.07 | 89.19 | 86.72 | 88.82 | 86.96 |

PSE = 1.02

| Variable | P Value |
| --- | --- |
| trt | <0.0001 |
| Time | <0.0001 |
| boar | 0.47 |
| trt*time | 0.8 |

TABLE 22

| Trt | DIA 0 h | DIA 24 h | DIA 48 h | DIA 72 h | DIA 96 h |
| --- | --- | --- | --- | --- | --- |
| Control | 8 | 12.1 | 14.29 | 15.26 | 15.61 |
| 1 mM | 8.83 | 12.79 | 14.92 | 13.35 | 14.35 |
| 5 mM | 8.01 | 11.42 | 12.78 | 11.72 | 10.82 |
| 10 mM | 7.29 | 10.55 | 11.68 | 10.58 | 10.49 |
| 25 mM | 6.68 | 9.82 | 11.34 | 11.07 | 14.39 |
| 50 mM | 6.33 | 8.7 | 10.33 | 9.04 | 10.5 |

PSE = 0.81

| Variable | P Value |
| --- | --- |
| trt | <0.0001 |
| Time | <0.0001 |
| boar | <0.0001 |
| trt*time | 0.21 |

Example 7

The following Example compares the post-sort viability of cryopreserved bovine semen when using TRIS-based low sugar media ("Low Sugar" treatment) or TRIS-based media containing a sugar additive ("Control"), as the sheath media and the catch media.

Semen from five bulls was collected and transported to a sorting facility in a TRIS-based holding media. The semen was prepared for sorting on the same day as collection. Semen was sorted as follows. In the Low Sugar treatment, the TRIS-based sheath media and the TRIS-based catch media comprised 10 mM glucose. In the Control, the TRIS-based sheath media comprised 78 mM of fructose and the TRIS-based catch media comprised 56 mM of fructose. After sorting, sperm was cryopreserved in AI straws. Cryopreserved straws (n=10/treatment) were thawed and analyzed for total motility and progressive motility via CASA. Straws with the highest, lowest and median values for total motility were pooled and analyzed for viability from a PI/PNA analysis on a flow cytometer. Post-thaw viability for the Low Sugar treatment was 67.53% and for the Control was 62.79% (P Value<0.02, and bull P Value<0.0001).

As can be easily understood from the foregoing, the basic concepts of the present invention may be embodied in a variety of ways. The invention involves numerous and varied embodiments using sex sorted sperm to increase the genetic progress of a line, including, but not limited to, the best mode of the invention.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

The following embodiments of the invention are presented by way of example only and do not limit the scope of the invention:

A. A method of processing sperm comprising the steps of:
   forming a stream comprising sperm and a first media;
   determining a property of said sperm in said stream;
   selecting sperm having a property of interest; and
   collecting said sperm having said property of interest in a second media, wherein said second media comprises less than about 20 mM of sugar additive.
B. The method of embodiment A, wherein said second media comprises less than about 15 mM of sugar additive.
C. The method of embodiment B, wherein said second media comprises less than about 10 mM of sugar additive.
D. The method of embodiment C, wherein said second media comprises less than about 5 mM of sugar additive.
E. The method of embodiment D, wherein said second media comprises less than about 20 ppm of sugar additive.
F. The method of embodiment E, wherein said second media comprises no sugar additive.
G. The method of embodiment A, wherein said first media is sheath fluid comprising less than about 20 mM of sugar additive.
H. The method of embodiment A, wherein said sperm are porcine sperm.
I. The method of embodiment A, wherein said sperm are bovine sperm.
J. The method of embodiment A, wherein said sperm are equine sperm.
K. The method of embodiment A, wherein said sperm are cervine sperm.
L. The method of embodiment A, wherein said sperm are ovine sperm.
M. The method of embodiment A, wherein the step of selecting sperm having a property of interest comprises photo-damaging said sperm having said property of interest.
N. The method of embodiment A, wherein the step of selecting sperm having a property of interest comprises isolating said sperm having said property of interest.
O. A method of processing sperm comprising the steps of:
   forming a stream comprising sperm and a first media, wherein said first media is sheath fluid comprising between about 0.1 ppm to about 20 mM of sugar additive;
   determining a property of said sperm in said stream;
   selecting sperm having a property of interest from said sperm in said stream; and
   collecting said sperm having said property of interest in a second media.
P. The method of embodiment O, wherein said first media comprises between about 0.1 ppm to about 15 mM of sugar additive.
Q. The method of embodiment P, wherein said first media comprises between about 0.1 ppm to about 10 mM of sugar additive.
R. The method of embodiment Q, wherein said first media comprises between about 0.1 ppm to about 5 mM of sugar additive.
S. The method of embodiment R, wherein said first media comprises between about 0.1 ppm to about 1 mM of sugar additive.
T. The method of embodiment S, wherein said first media comprises between about 0.1 ppm to 20 ppm of sugar additive.
U. The method of embodiment O, wherein said second media comprises less than about 20 mM of sugar additive.
V. The method of embodiment O, wherein said sperm are porcine sperm.
W. The method of embodiment O, wherein said sperm are bovine sperm.
X. The method of embodiment O, wherein said sperm are equine sperm.
Y. The method of embodiment O, wherein said sperm are cervine sperm.
Z. The method of embodiment O, wherein said sperm are ovine sperm.
AA. The method of embodiment O, wherein the step of selecting sperm having a property of interest from said sperm in said stream comprises photo-damaging said sperm having said property of interest.
AB. The method of embodiment O, wherein the step of selecting sperm having a property of interest from said sperm in said stream comprises isolating said sperm having said property of interest.
AC. The method of embodiments A or O, wherein said first media or said second media comprise one or more OSRs.
AD. The method of embodiment AC, wherein the one or more OSRs is selected from the following: catalase, SOD, an SOD mimic, glutathione, glutathione reductase, glutathione peroxidase, pyruvate, mercaptoethanol, BHT, lipoic acid, flavins, quinines, vitamin K (and related vitamers), vitamin B12, vitamin B12 vitamers, vitamin E (and related vitamers), tocopherols, tocotrienols, α-tocopheryl, alpha ketoglutarate (AKG), malondialdehyde (MDA), asymmetric dimethylarginine (ADMA) and biologically active derivatives thereof.
AE. The method of embodiment AD, wherein the one or more OSRs is in the concentration range of 0.01 mg/ml to 5 mg/ml.
AF. The method of embodiments A or O, further comprising the step of resuspending at least one of the one or more subpopulations in a third media less comprising than about 20 mM of sugar additive.
AG. The method of embodiment AF, wherein said third media comprises one or more OSRs.
AH. The method of embodiments A or O, further comprising the step of fertilizing an egg with sperm having said desired characteristic or inseminating a female with sperm having said desired characteristic.
AI. A method of processing sperm comprising
   freezing and thawing a media comprising less than 20 mM of sugar additive and a protein source; and
   contacting sperm with said media.

AJ. The method of embodiment AI, wherein the protein source comprises egg yolk.

AK. A composition comprising sperm and a media comprising less than 20 mM of sugar additive and a protein source, wherein said media has been frozen and thawed prior to addition of said sperm.

AL. The composition of embodiment AK, wherein said protein source comprises egg yolk.

AM. The composition of embodiment AL, wherein said sperm are a gender enriched sperm population.

AN. A composition comprising a gender enriched sperm population and a media comprising less than 20 mM of sugar additive.

AO. The composition of embodiment AN, wherein said media comprises less than about 15 mM of sugar additive.

AP. The composition of embodiment AO, wherein said media comprises less than about 10 mM of sugar additive.

AQ. The composition of embodiment AP, wherein said media comprises less than about 5 mM of sugar additive.

AR. The composition of embodiment AQ, wherein said media comprises less than about 20 ppm of sugar additive.

AS. The composition of embodiment AR, wherein said media comprises no sugar additive.

AT. The composition of embodiment AN, further comprising a protein source.

AU. The composition of embodiment AT, wherein said protein source is egg yolk.

AV. A method of processing sperm comprising the steps of:
diluting sperm in a first media comprising less than 20 mM of sugar additive;
forming a stream comprising said sperm;
determining a property of said sperm in said stream;
selecting sperm having a property of interest from said sperm in said stream; and
collecting said sperm having said property of interest in a second media.

AW. The method of embodiment AV, wherein said first media comprises less than about 15 mM of sugar additive.

AX. The method of embodiment AW, wherein said first media comprises less than about 10 mM of sugar additive.

AY. The method of embodiment AX, wherein said first media comprises less than about 5 mM of sugar additive.

AZ. The method of embodiment AY, wherein said first media comprises less than about 20 ppm of sugar additive.

BA. The method of embodiment AZ, wherein said first media comprises no sugar additive.

BB. The method of embodiment AV, wherein said second media comprises less than about 20 mM of sugar additive.

BC. The method of embodiment AV, wherein said sperm are porcine sperm.

BD. The method of embodiment AV, wherein said sperm are bovine sperm.

BE. The method of embodiment AV, wherein said sperm are equine sperm.

BF. The method of embodiment AV, wherein said sperm are deer sperm.

BG. The method of embodiment AV, wherein the step of selecting sperm having a property of interest from said sperm in said stream comprises photo-damaging said sperm having said property of interest.

BH. The method of embodiment AV, wherein the step of selecting sperm having a property of interest from said sperm in said stream comprises isolating said sperm having said property of interest.

What we claim is:

1. A method of processing sperm comprising the steps of:
forming a stream comprisingسperm and a sheath fluid;
determining a property of said sperm in said stream;
selecting sperm having a property of interest; and
collecting said sperm having said property of interest in a catch media that does not contain a sugar additive, wherein said catch media comprises egg yolk at a concentration of about 16.7% and wherein said catch media is frozen and thawed prior to said step of collecting.

2. The method of claim 1, wherein the step of selecting sperm having a property of interest comprises photo-damaging said sperm having said property of interest.

3. The method of claim 1, wherein the step of selecting sperm having a property of interest comprises isolating said sperm having said property of interest.

4. The method of claim 1, wherein said sheath fluid or said catch media comprise one or more organic stress reducing agents (OSRs).

5. The method of claim 4, wherein the one or more OSRs is selected from the following: catalase, SOD, an SOD mimic, glutathione, glutathione reductase, glutathione peroxidase, pyruvate, mercaptoethanol, BHT, lipoic acid, flavins, quinines, vitamin K (and related vitamers), vitamin B12, vitamin B12 vitamers, vitamin E (and related vitamers), tocopherols, tocotrienols, α-tocopheryl, alpha ketoglutarate (AKG), malondialdehyde (MDA), asymmetric dimethylarginine (ADMA) and biologically active derivatives thereof.

6. The method of claim 5, wherein the one or more OSRs is in the concentration range of 0.01 mg/ml to 5 mg/ml.

7. The method of claim 1, further comprising the step of resuspending at least one of the one or more subpopulations in a resuspension media comprising 1 mM to 10 mM of a sugar additive.

8. The method of claim 7, wherein said resuspension media comprises one or more OSRs.

9. The method of claim 1, further comprising the step of fertilizing an egg with sperm having said property of interest or inseminating a female with sperm having said property of interest.

* * * * *